(12) United States Patent
Satoh et al.

(10) Patent No.: US 7,415,757 B2
(45) Date of Patent: Aug. 26, 2008

(54) METHOD FOR MANUFACTURING INDUCTOR HAVING COIL EMBEDDED DUST CORE

(75) Inventors: Sadaki Satoh, Tokyo (JP); Junetsu Tamura, Tokyo (JP); Hideharu Moro, Tokyo (JP); Tsuneo Suzuki, Tokyo (JP)

(73) Assignee: TDK Corporation, Tokyo (JP)

( * ) Notice: Subject to any disclaimer, the term of this patent is extended or adjusted under 35 U.S.C. 154(b) by 525 days.

(21) Appl. No.: 11/140,348

(22) Filed: May 26, 2005

(65) Prior Publication Data

US 2005/0219027 A1    Oct. 6, 2005

Related U.S. Application Data

(62) Division of application No. 10/392,322, filed on Mar. 19, 2003, now abandoned.

(30) Foreign Application Priority Data

Mar. 20, 2002   (JP)   ............................. 2002-079044

(51) Int. Cl.
*H01F 7/06* (2006.01)
(52) U.S. Cl. ........................... 29/602.1; 29/605; 29/606; 336/200; 336/90
(58) Field of Classification Search ................ 29/602.1, 29/605, 609, 606, 729, 739; 336/83, 90, 336/98, 192, 200, 223; 264/113, 125, 272.19
See application file for complete search history.

(56) References Cited

U.S. PATENT DOCUMENTS

| | | | |
|---|---|---|---|
| 6,759,935 B2 | 7/2004 | Moro et al. | ..................... 336/83 |
| 6,791,445 B2 | 9/2004 | Shibata et al. | ................ 336/90 |
| 6,940,387 B2 * | 9/2005 | Shibata et al. | ............... 336/200 |
| 2003/0214379 A1 | 11/2003 | Satoh et al. | .................. 336/200 |

FOREIGN PATENT DOCUMENTS

| | | |
|---|---|---|
| JP | 57-128014 | 8/1982 |
| JP | 04-165605 | 6/1992 |
| JP | 04-286305 | 10/1992 |
| JP | 05-291046 | 11/1993 |
| JP | 11-273980 | 10/1999 |
| JP | 2001-267160 | 9/2001 |

* cited by examiner

*Primary Examiner*—Minh Trinh
(74) *Attorney, Agent, or Firm*—Hogan & Hartson LLP

(57) ABSTRACT

A method for manufacturing a coil-embedded dust core with a small variation in inductance value with efficiency includes a step (a) of charging soft magnetic metal powder including an insulating material, composing a green body 10, so as to cover a coil 1, and (b) compacting the soft magnetic metal powder covering the coil 1 in an axial direction of the coil 1. In the step (b), the soft magnetic metal powder is compacted while an amount of the soft metal powder charged into the part corresponding to the winding section is kept smaller than an amount of the soft magnetic metal powder charged into the other part that are not corresponding to the winding section, with an upper surface or a lower surface of the winding section as a reference.

7 Claims, 15 Drawing Sheets

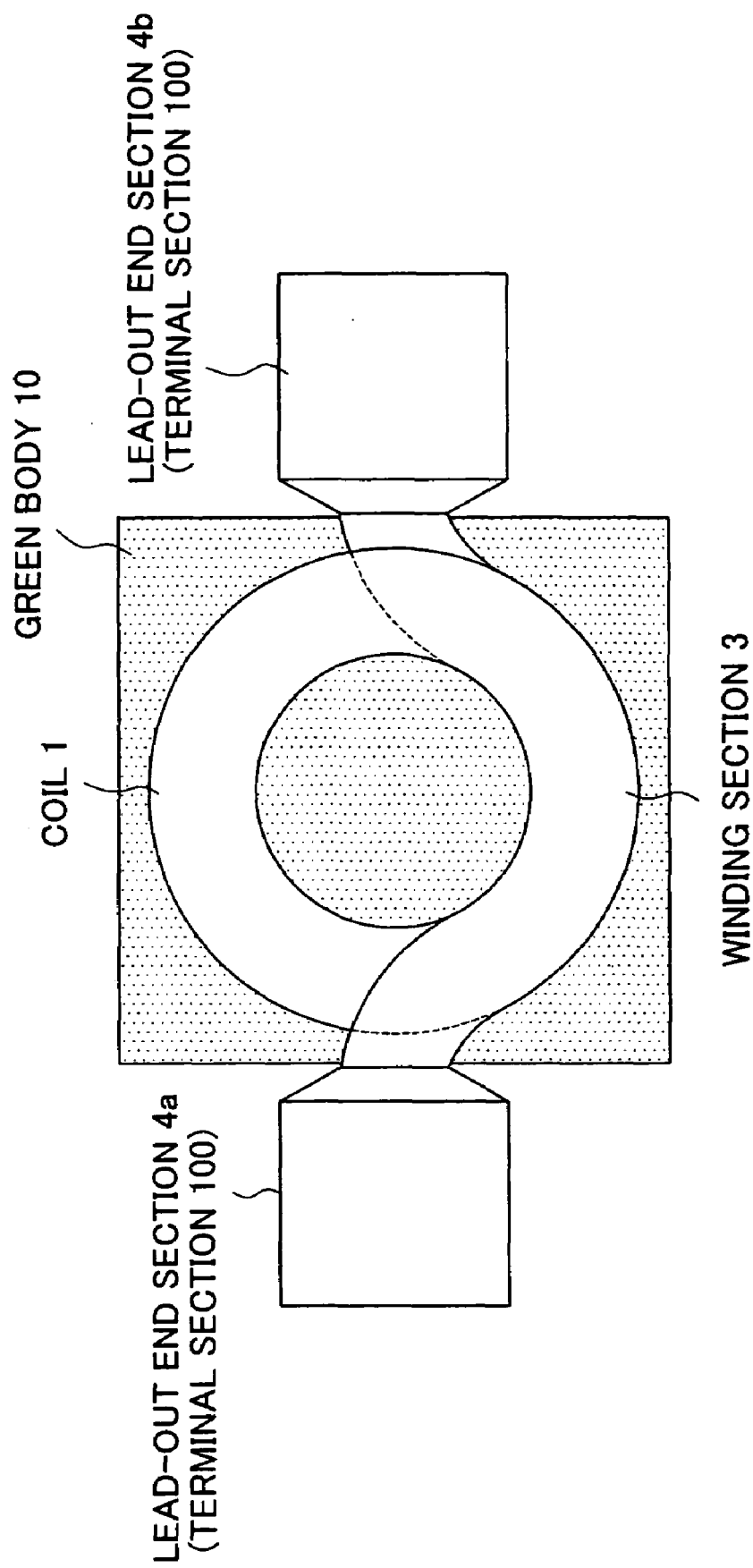

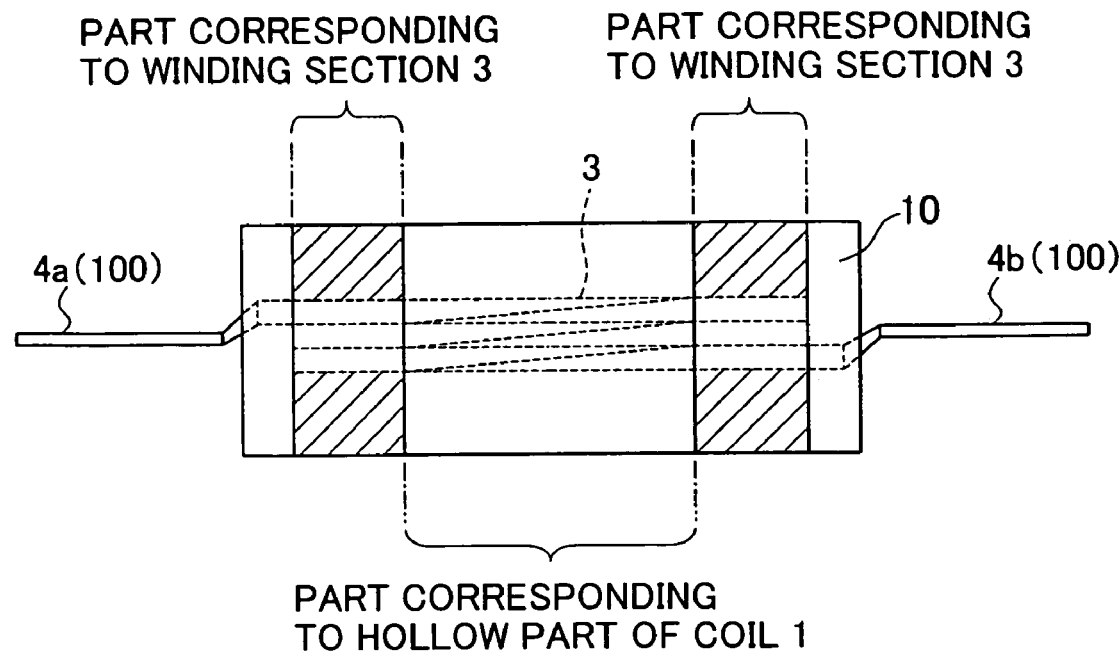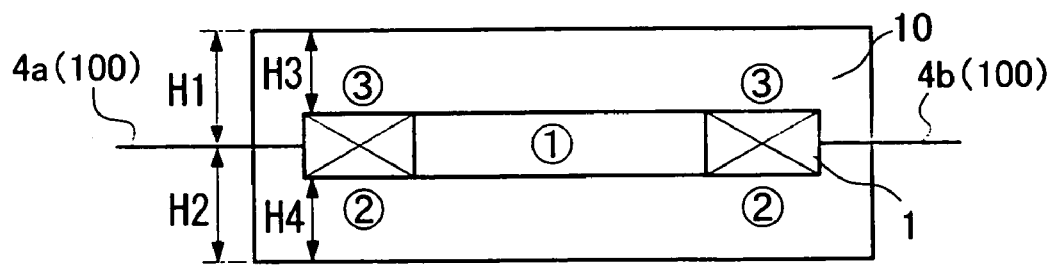

CROSS SECTION AFTER WINDING

CROSS SECTION BEFORE WINDING

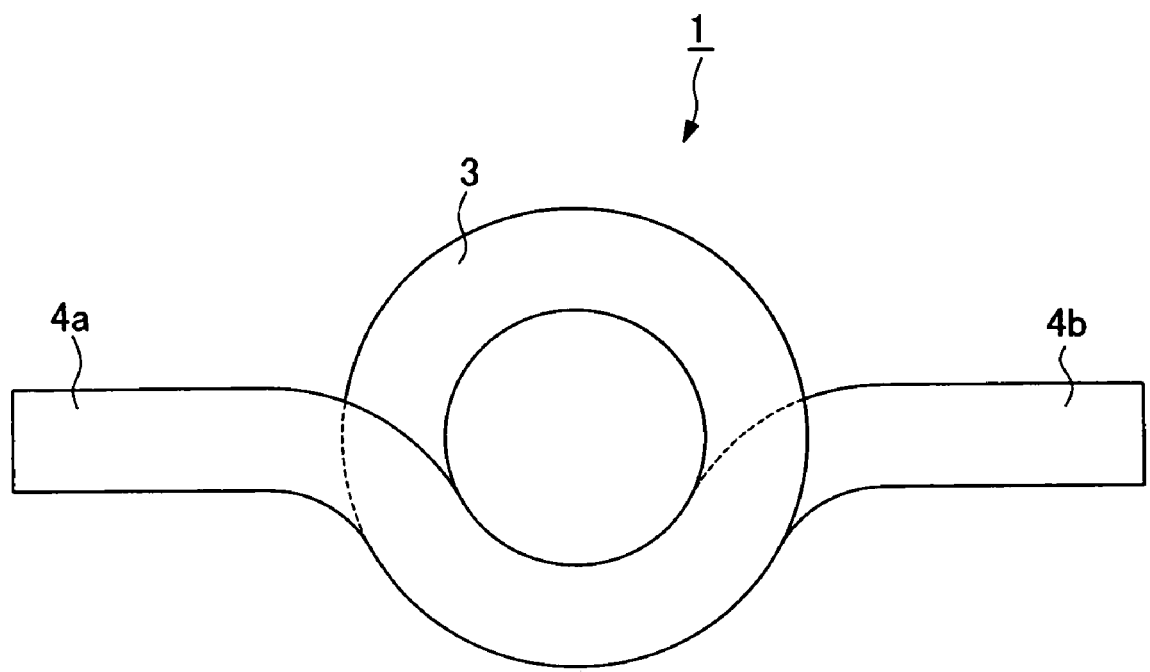

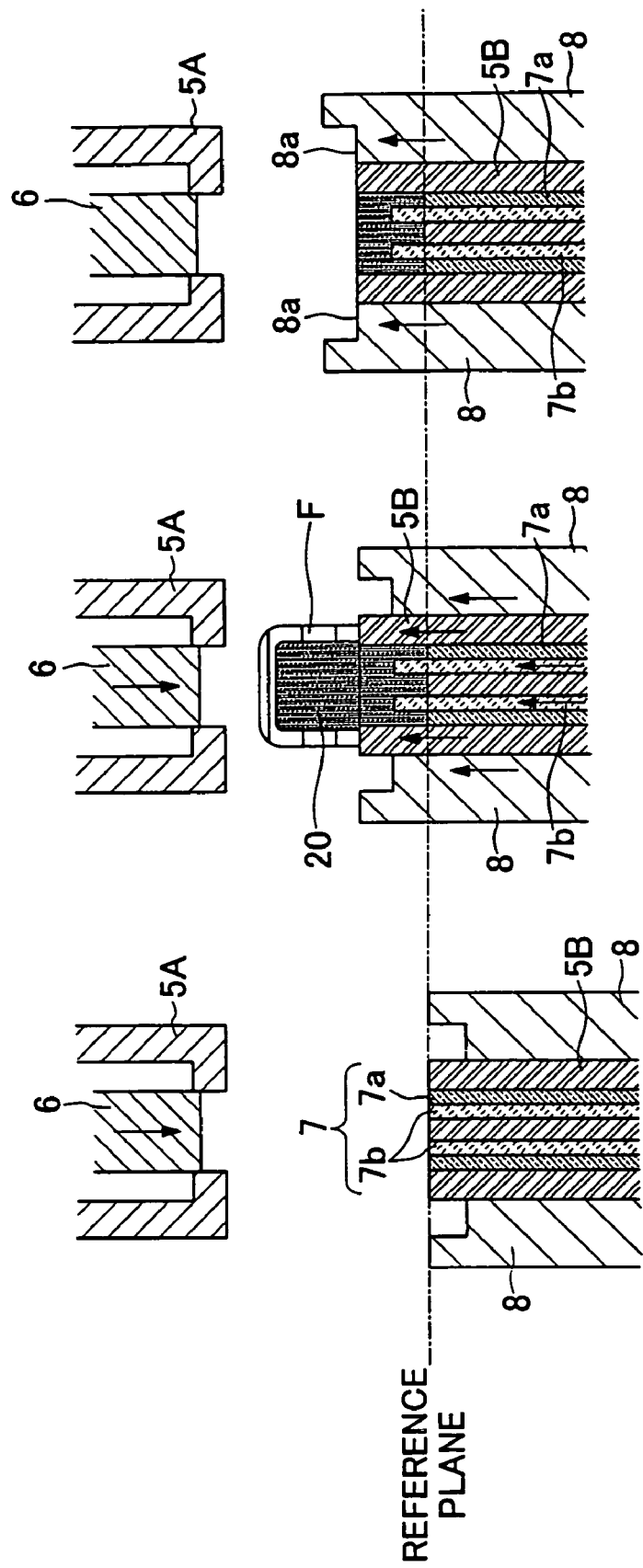

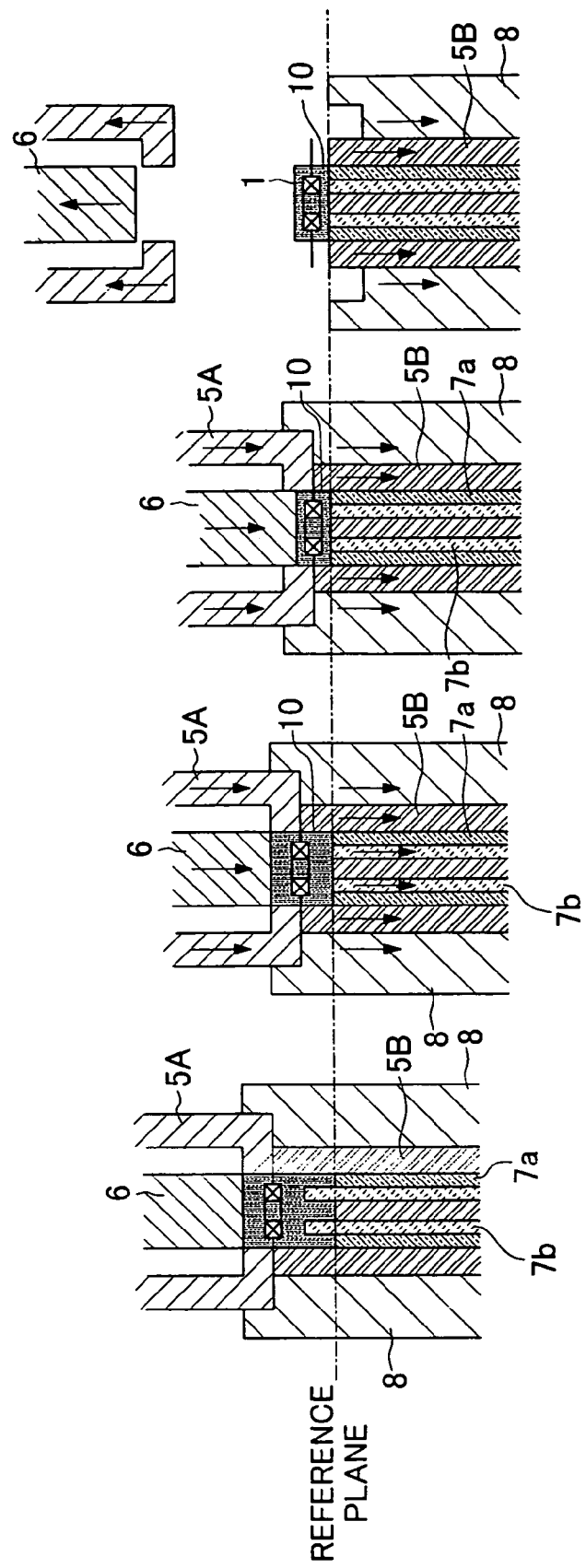

PRESENT INVENTION

CONVENTIONAL METHOD (WITH PREFORMING)

CONVENTIONAL METHOD (WITHOUT PREFOMING)

METHOD FOR MANUFACTURING INDUCTOR HAVING COIL EMBEDDED DUST CORE

This is a divisional of application Ser. No. 10/392,322 filed Mar. 19, 2003, now abandoned which application is hereby incorporated by reference in its entirety.

BACKGROUND OF THE INVENTION

1. Field of the Invention

The present invention relates to a coil-embedded dust core, which may be used in inductors having a unitary structure with a magnetic core and in other electronic components. The present invention also relates to a method for manufacturing the coil-embedded dust core. More particularly, the invention relates to a method for manufacturing coil-embedded dust core constructed by embedding an air-core coil in a green body, and the like.

2. Description of the Related Art

In recent years, electric and electronic equipment has become more compact, and dust cores that are compact (low in height) yet able to accommodate large current have come to be in demand.

Materials used for dust cores are ferrite powder and ferromagnetic metal powder, but ferromagnetic metal powder has larger saturation magnetic flux density than ferrite powder and its DC bias characteristics may be maintained even in a strong magnetic field. Consequently, in making a dust core that can accommodate large current, using ferromagnetic metal powder as a material for dust core has become mainstream.

In addition, in order to further the effort to make the core more compact (lower in height), a coil body in which a coil and compacted magnetic powder form a unitary structure has been proposed. In the present specification, an inductor having such a structure may be called a "coil-embedded dust core."

A manufacturing method for a surface-mount type inductor having a structure of a coil-embedded dust core has been proposed in the past. For example, Japanese Patent Laid-Open No. 5-291046 discloses that an exterior electrode is connected to an insulation-coated conduction wire, and these are enclosed in magnetic powder, which is then compressed into a magnetic body. Japanese Patent Laid-Open No.11-273980 discloses that a composite material made by mixing flat soft magnetic metal powder and binder, and a coil are inserted into a die constituted by a die set and a bottom punch at the same time and compression-forming is performed. Japanese Patent No. 2958807 discloses a method for manufacturing an inductor by compressing magnetic powder while orientating the easy axis of magnetization of magnetic powder along the orientation of the magnetic field formed by energizing the coil in order to obtain a large inductance value. Further, Japanese Patent No.3108931 discloses the method for manufacturing an inductor by preparing a first green body and a second green body which are preformed by compression respectively and by performing main compression-forming until an interface between the first green body and the second green body is removed with the coil being vertically sandwiched with these green bodies. According to the method described in Japanese Patent No. 3108931, a loading weight of magnetic powder constituting the green body can be increased, and therefore a larger inductance value can be obtained than in the above-described Japanese Patent Laid-Open No. 5-291046, Japanese Patent Laid-Open No. 11-273980, and Japanese Patent No. 2958807.

However, according to the method described in Japanese Patent No. 3108931, three forming operations are required, that is, performing of the first green body, performing of the second green body, and main forming performed with the coil being sandwiched by the first green body and the second green body. When these forming operations are performed with one die machine, a die has to be replaced for each forming operation, which is inefficient. Further, in the case of main forming, compressing pressure is increased so that the interface of the preformed core is not left, which causes problems of deformation of the coil, an insulation failure and the like.

As described above, a large inductance value can be obtained with the coil-embedded dust core of a small size, and while size reduction of electric and electronic devices are rapidly advancing, there is a strong demand for improvement in quality of the coil-embedded dust core. In concrete, as the frequency at which the coil-embedded dust core is used is shifted to a higher frequency side, the demand for precision of the inductance values increases. Since impedance increases in proportion to a frequency, the coil-embedded dust core has to be designed so that the inductance value decreases as the frequency, at which the coil-embedded dust core is used, is shifted to a higher frequency side. Meanwhile, it is necessary to avoid the situation in which part of the magnetic body is saturated magnetically and a predetermined inductance value (design value) cannot be obtained. Namely, it is required to obtain an inductance value previously specified based on the working frequency with stability.

Thus, in view of the above-described points, the present invention has its object to provide a method for efficiently manufacturing a coil-embedded dust core which attains a predetermined inductance value (design value) with a small variation in inductance value, and the like.

SUMMARY OF THE INVENTION

When the inventors made various studies to solve the above-described problems, the inventor found out that the position of the coil in the coil-embedded dust core and the position especially in the compacting direction have a large influence on inductance, and a variation of the inductance value is reduced by entirely equalizing the density of the green body. The inventors also confirm that it is easy and effective to reduce the amount of soft magnetic metal powder charged into the part corresponding to the winding section of the air-core coil more than the amount of the soft magnetic metal powder charged into the other part which is not corresponding to the winding section in order to equalize the density of the green body in the coil-embedded dust core entirely. Namely, the present invention is a method for manufacturing a coil-embedded dust core constructed by embedding an air-core coil having a winding section and end sections led out of the winding section in a green body, and characterized by including a step (a) of charging soft magnetic metal powder including an insulating material, composing the green body, so as to cover the air-core coil, and a step (b) of compacting the soft magnetic metal powder covering the air-core coil in an axial direction of the air-core coil, and characterized in that in the step (b), the soft magnetic metal powder is compacted while an amount of the soft metal powder charged into a part corresponding to the winding section is kept smaller than an amount of the soft magnetic metal powder charged into the other part that are not corresponding to the winding section, with an upper surface or a lower surface of the winding section as a reference.

Here, as the other part, the part corresponding to the hollow part of the air-core coil is cited. Namely, compacting is performed in the state in which more soft metal powder is charged into the part corresponding to the hollow part of the air-core coil than the part corresponding to the winding section. It is also preferable to charge a larger amount of soft magnetic metal powder into the parts corresponding to the corner parts of the green body and the surroundings of the end sections led out form the winding section than into the part corresponding to the winding section. Since the soft magnetic metal powder charged into the part corresponding to the winding section of the air-core coil (hereinafter, appropriately called "a coil part") is easily compacted than the soft magnetic metal powder charged into the other part which is not corresponding to the winding section (hereinafter, appropriately called "a non-coil part"), the density of the coil part inevitably tends to be higher than that of the non-coil part, but by performing compacting in the state in which more soft magnetic metal powder is charged into the non-coil part than into the coil part in advance, the coil-embedded dust core with entirely uniform density can be obtained. According to the coil-embedded dust core with entirely uniform density, a variation in inductance value is reduced, and it becomes possible to obtain a predetermined inductance value with stability. Since the coil is metal, it is more difficult to compress than soft magnetic metal powder, and the coil is sometimes damaged if it is forcefully pressurized. However, according to the method proposed by the present invention, the coil-embedded dust core with entirely uniform density can be obtained without damaging the coil.

In the aforementioned step (b), a compression ratio of the soft magnetic metal powder in a part corresponding to the maximum number of windings out of the winding section and a compression ratio of the soft magnetic metal powder in the other part can be made equal. When an air-core coil is made by winding, for example, a conductor 2.5 turns in order to form the terminals at both sides of the component; there exist a three-turn part and a two-turn part. In this case, the three-turn part becomes the part corresponding to the maximum number of windings, and the compression ratio of this part is usually the highest, but according to the present invention, it becomes possible to equalize the compression ratios of the soft magnetic metal powder of the part corresponding to the maximum number of windings out of the winding section and the other part, for example, the non-coil part such as the part corresponding to the hollow part of the coil. Here, the compression ratio in this specification is the ratio of the thicknesses of the soft magnetic metal powder before and after compression.

According to the method for manufacturing the coil-embedded dust core according to the present invention, a density of the green body in the vicinity of an upper surface or a lower surface of the part corresponding to the maximum number of windings out of the winding section and a density of the green body in the other part can be made equal.

Further, the present invention provides a method for manufacturing a coil-embedded dust core in which an air-core coil is embedded in a green body with use of a die machine comprising a upper die set including an upper die and a top punch ascending and descending inside the upper die, and a lower die set including a lower die and a bottom punch ascending and descending inside the lower die. In concrete, in a step (a), soft magnetic metal powder including an insulation material, composing the green body, is charged into a cavity of the lower die equipped with a tubular member, which has a top portion in substantially the same shape as the plane shape of the air-core coil, in the bottom punch to be ascendable and descendable. In the following step (b), the air-core coil is placed concentrically with the tubular member in a state in which it ascends to a predetermined position, inside the cavity of the lower die with the soft magnetic metal powder being charged therein, and in a step (c), the upper die descends to the lower die, and further charging the soft magnetic metal powder into a cavity of the upper die so as to cover the air-core coil. In a step (d), the soft magnetic metal powder is compacted in the axial direction of the air-core coil by relatively lowering the top punch with respect to the bottom punch. Here, the air-core coil can be a coil made by winding a flat conductor, including a winding section being insulation coated and end sections led out of the winding section. With use of the coil with the flat conductor being wound around, the current capacity per volume can be increased, and further reduction in size of the coil-embedded dust core (reduction in height) is made possible.

Prior to the aforementioned step (a), it is effective to further include a step of controlling a relative position of the lower die, the bottom punch and the tubular member in a compacting direction according to thickness of the winding section of the air-core coil in the axial direction. This makes it possible to place the air-core coil at the center in the axial direction of the green body ultimately.

Further, in the aforementioned step (d), it is desired that the upper die, the lower die and the tubular member relatively descend to a predetermined position with respect to the bottom punch while a state in which the end sections of the air-core coil are held between the upper die and the lower die is kept, and in synchronism with the movement to relatively lower the top punch with respect to the bottom punch. This makes it possible to pressurize the soft magnetic metal powder in the vertical direction without damaging the end sections of the air-core coil.

Furthermore, the present invention provides a coil-embedded dust core including a green body in a rectangular parallelepiped shape having a front and back surfaces opposed to each other with a predetermined distance and a side surface formed on perimeters of the front and back surfaces, and an air-core coil having a winding section and end sections led out from the winding section, with at least the winding section being placed in the green body, and characterized in that densities of the green body are equal in a part corresponding to a maximum number of windings out of the winding section and in a hollow part of the air-core coil. According to the coil-embedded dust core according to the present invention, a difference in density between the part corresponding to the maximum number of windings out of the winding section and the hollow part of the air-core coil can be made only 0.3 $g/cm^3$ or less, whereby the coil-embedded dust core with a small variation in inductance value can be ultimately obtained.

It is desirable that the air-core coil is constructed by a rectangular wire. Further, it is effective to use a so-called terminal-integrated air-core coil, in which part of the air-core coil functions as a terminal section. Furthermore, the end sections of the air-core coil can be exposed to an outside of the green body from a center of side surface of the green body with a thickness direction of the green body as the reference. If the connection part is located inside the green body, a joint failure (including joint failure) easily occurs to the connection part during compression, and by making the end sections of the air-core coil as the terminal section, and exposing the end sections to the outside of the green body, the connection part can be placed outside. Thus, the coil-embedded dust core can be provided which hardly causes problems such as joint failure between the coil and the terminal section or insulation failure of the coil and terminal section with respect to the magnetic powder. In this specification, the connection part means the portion at which the components are electrically connected to each other, and the portion at which soldering is made with the external electrode such as a land pattern of the surface mounting substrate is called a terminal section. In order to expose the end sections of the air-core coil to the outside of the green body from the center of the side surface of the green body with the thickness direction of the green body as a reference, it may be suitable to carry out the method for manufacturing the coil-embedded dust core proposed by the present invention with use of the coil with the flat conductor being wound around and with its both end sections being formed on the same plane.

BRIEF DESCRIPTION OF THE DRAWINGS

FIG. 1 is a cross-sectional top view of a coil-embedded dust core in accordance with an embodiment;

FIGS. 2A and 2B are sectional side views of a coil-embedded dust core in accordance with an embodiment;

FIG. 8 is a view for illustrating a forming step;

FIGS. 13A to 13C are views explaining the compressing step in step S206 in FIG. 11;

FIGS. 15A to 15D are views explaining the compressing step in step S206 in FIG. 11.

DETAILED DESCRIPTION OF THE PREFERRED EMBODIMENTS

The present invention is described in detail below with reference to an embodiment shown in the accompanying drawings.

Figure 3:
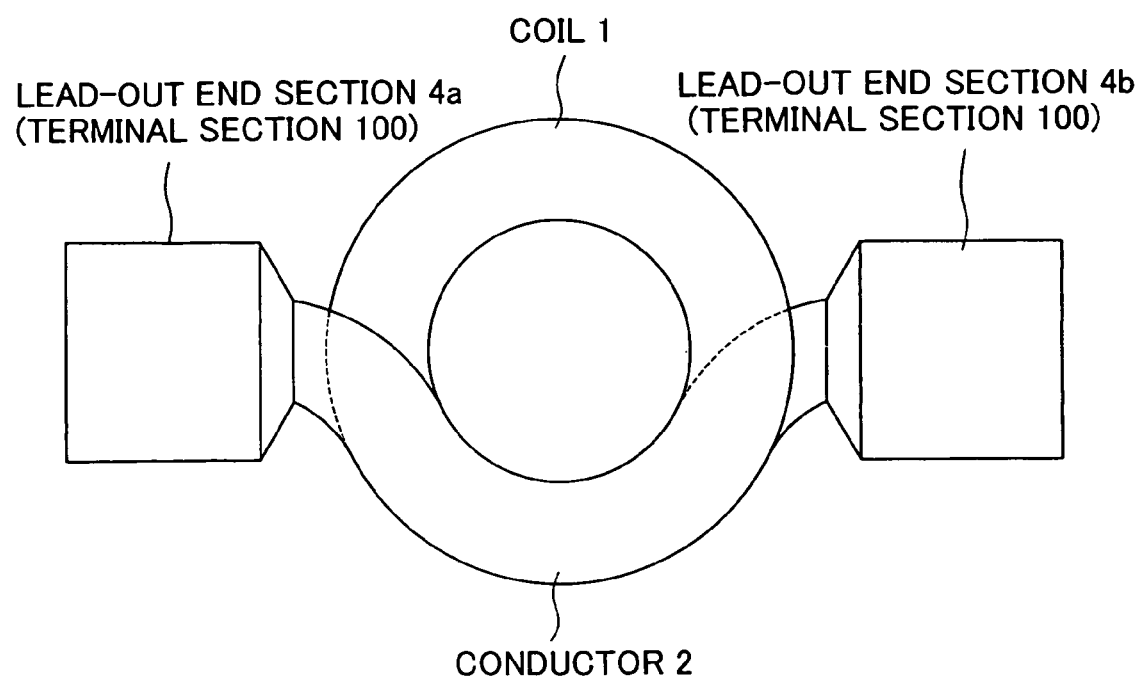
FIG. 3 is a plan view of a coil to be used in an embodiment.
Figure 4:
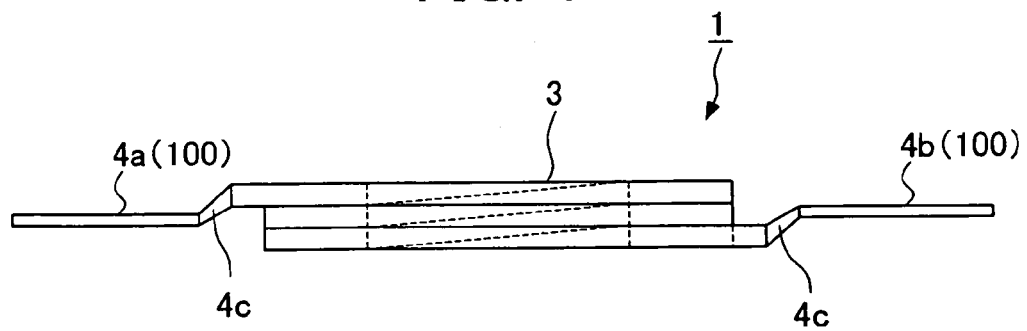
FIG. 4 is a side view of a coil used in an embodiment.

FIG. 1 is a cross-sectional top view of a coil-embedded dust core according to this embodiment. FIG. 2A and FIG. 2B are sectional side views of the coil-embedded dust core, and FIG. 2B shows a simplified view of FIG. 2A. FIG. 3 is a plan view of a coil (air-core coil) 1 used in this embodiment, and FIG. 4 is a side view of the coil 1. As shown in FIGS. 1 to 4, the coil 1 is an air-core coil including a winding section 3 in which a flat conductor 2 is wound and laminated and lead-out end sections 4a and 4b each of which is extended from the winding section 3. A green body 10 covers the coil 1 and its circumference except the lead-out sections 4a and 4b of the coil 1. Although a detailed description is given later, in this embodiment, the coil 1 is of what is called a terminal integrated construction so that the lead-out end sections 4a and 4b of the coil 1 function as a terminal section 100.

As described above, the coil-embedded dust core in the present embodiment is characterized in that the densities of a part corresponding to the winding section 3 of the coil 1 (coil part) and a non-coil part (a part corresponding to a hollow part of the coil 1, a part corresponding to corner parts of a green body 10, and surroundings of end sections led out from the winding section 3) are uniform. Here, as shown in FIG. 2A, the part corresponding to the winding section 3 of the coil 1 is the part corresponding to an upper surface and a lower surface of the winding section 3 in the green body 10 with an axial direction of the coil 1 (thickness direction) as a reference. The part corresponding to the hollow part of the coil 1 is the hollow part of the coil 1, and the part which is the hollow part of the coil 1 extended to the upper surface and the lower surface of the green body 10 in the axial direction.

One of the characteristics of the coil-embedded dust core in this embodiment is that the coil 1 is accurately located at a center in the axial direction of the green body 10. Namely, as shown in FIG. 2B, in the coil-embedded dust core in this embodiment, a distance H1 from the lead-out end section 4a (4b) to the upper surface of the green body 10 and a distance H2 from the lead-out end section 4a (4b) to the lower surface of the green body 10 are equal. A distance H3 from the upper surface of the winding section 3 of the coil 1 to the upper surface of the green body 10 and a distance H4 from the lower surface of the winding section 3 of the coil 1 to the lower surface of the green body 10 are equal.

As described in detail in the embodiment below, in the coil-embedded dust core in this embodiment, the densities of the part corresponding to the winding section 3 of the coil 1 shown by ② and ③ in FIG. 2B and the part corresponding to the hollow part of the coil 1 shown by ① in FIG. 2B are equal.

First, the green body 10 is described.

The green body 10 is made by adding an insulating material to ferromagnetic metal powder, mixing them, and thereafter compressing them according to predetermined conditions. Also, it is preferable that after the ferromagnetic metal powder, to which the insulating material is added, is dried, a lubricant is added to the dried magnetic powder and they are mixed.

As the ferromagnetic metal powder used in the green body 10, single metal powder, two or more kinds of metal powder having a different chemical composition, or alloy powder can be used. The metal powder can be composed of any transition metal element exhibiting soft magnetism or an alloy consisting of a transition metal element and other metal elements. As a concrete example of soft magnetic metal, an alloy composed mainly of one or more kinds of Fe, Co and Ni can be cited. For example, Permalloy (Fe—Ni system alloy, Fe—Ni—Mo system alloy), Sendust (Fe—Si—Al system alloy), Fe—Si system alloy, Fe—Co system alloy, Fe—P system alloy, and the like are preferable. Among these, Permalloy is suitable because of its high magnetic permeability and excellent workability.

When an Fe—Ni system alloy (Permalloy) is selected as ferromagnetic metal powder used in the green body 10, the chemical composition should be 15 to 60 wt % of Fe and 40 to 85 wt % of Ni. Also, an Fe—Ni—Mo system alloy (Permalloy) is selected as ferromagnetic metal powder used in the green body 10, the chemical composition should be 15 to 30 wt % of Fe, 70 to 85 wt % of Ni, and 1 to 5 wt % of Mo.

The shape of particle of ferromagnetic metal powder used in the green body 10 is not limited, a powder with spherical or elliptical particles is preferably used.

The ferromagnetic metal powder may be obtained by the gas atomizing method, water atomizing method, rotary disk method, etc.

By adding the insulating material, the ferromagnetic metal powder is insulation-coated. The insulating material is properly selected depending on the properties of the magnetic core required, and some of the materials that may be used as an insulating material are various organic polymer resins, silicone resin, phenolic resin, epoxy resin, and water glass; moreover, a mixture of one of these resins and inorganic substances may also be used.

The amount of the insulating material to be added varies depending on the properties of the magnetic core required, but approximately 1 to 10 wt % may be added. When the amount of the insulating material added exceeds 10 wt %, permeability falls and the loss tends to be larger. On the other hand, when the amount of the insulating material added is less than 1 wt %, there is a possibility of insulation failure. A desirable amount of insulating material added is 1.5 to 5 wt %.

The amount of the lubricant to be added may be approximately 0.1 to 1.0 wt %, the amount of the lubricant to be added may preferably be 0.2 to 0.8 wt %, but the more preferable amount of the lubricant to be added may be 0.3 to 0.8 wt %. When the amount of the lubricant added is less than 0.1 wt %, removing the die after compressing becomes difficult and cracks on the molded product are more likely to occur. On the other hand, when the amount of the lubricant added exceeds 1.0 wt %, density falls and permeability decreases.

The lubricant may be selected from among, for example, aluminum stearate, barium stearate, magnesium stearate, calcium stearate, zinc stearate and strontium stearate. Using aluminum stearate as the lubricant is desirable, due to the fact that its so-called spring back is small.

In addition, a predetermined amount of a cross-linking agent may be added to the ferromagnetic metal powder. Adding the cross-linking agent does not deteriorate the magnetic properties of the green body 10, and Instead increases its strength. The amount of the cross-linking agent to be added may preferably be 10 to 40 wt % to the insulating material such as silicone resin. The cross-linking agent may be organic titanium compounds.

Next, the construction of the coil 1 is described with reference to FIGS. 3 and 4.

As shown in FIGS. 3 and 4, the coil 1 is formed by having the conductor 2 wound 2.5 turns in edgewise winding, and the lead-out end section 4a, 4b of the conductor 2 has a construction such that the conductor 2 is extended from a body section of the coil 1 by inverse forming. That is, the coil 1 is formed integrally without joint.

The cross section of the conductor 2 that forms the coil 1 is flat. Some of the possible flat cross-sectional shapes are rectangular, trapezoidal, or elliptical, for example. The conductor 2 having a rectangular cross section may be formed by a rectangular wire made of an insulation-coated copper wire. When a rectangular wire is used as the conductor 2, the cross-sectional dimensions may preferably be approximately 0.1 to 1.0 mm long by 0.5 to 5.0 mm wide.

The insulation coating on the conductor 2 may normally be an enamel coating, and the enamel coating thickness may preferably be about 3 μm.

When the coil 1 is formed by winding the flat conductor 2, the layers of winding that makes up the coil 1 can be brought into very close contact with each other as shown in FIG. 4. Consequently, the electric capacity per cubic volume can be improved, and a product with a smaller height can be provided as compared with the case where a conductor having a circular cross section is used. In addition, the wire occupation rate can be improved significantly as compared with the case where the coil 1 is formed by winding a conductor whose number of turns is equal but whose cross section is circular.

Therefore, the coil 1 made by winding the flat conductor 2 is favorable in making a coil-embedded dust core for a large current.

FIG. 5 shows the cross-sectional shapes of the flat conductor 2 before and after winding.

Figure 5B:
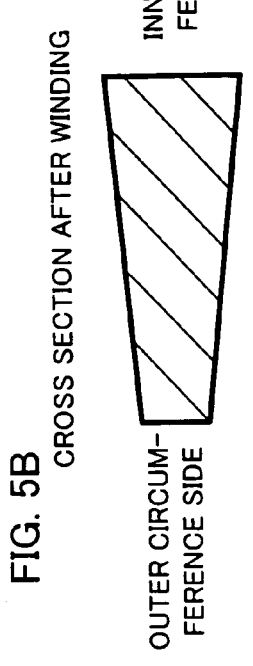
FIGS. 5A to 5D are schematic views showing cross-sectional shapes before and after a flat conductor is wound.
Figure 5D:
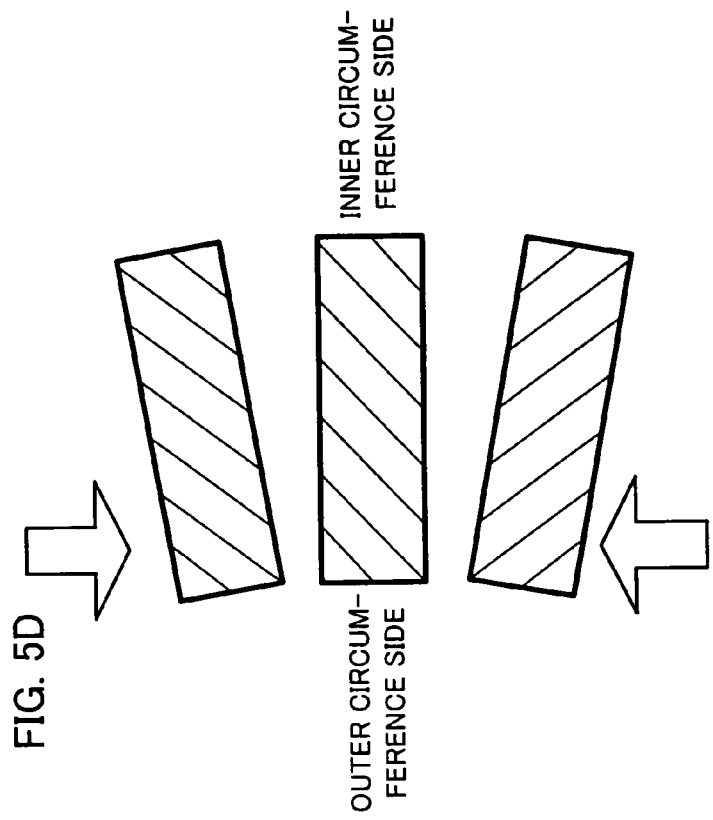
Figure 5A:
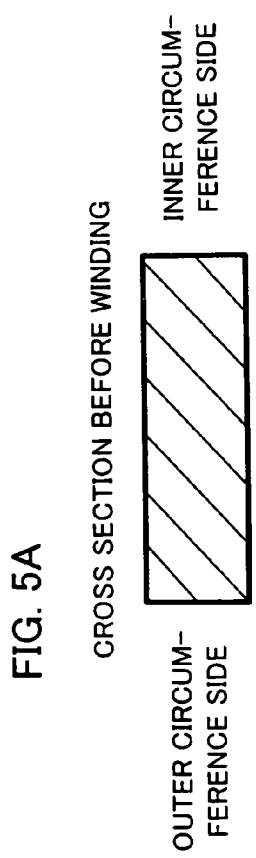

When a rectangular wire is used as the flat conductor 2, the thickness of cross section before winding the conductor 2 is uniform as shown in FIG. 5A. When the conductor 2 is wound from this state, its thickness on the outer circumference side (on the outside of the winding) of the coil 1 becomes smaller than its thickness on the inner circumference side (on the inside of the winding) as shown in FIG. 5B. Here, as described above, the coil 1 is formed by winding the conductor 2 a few turns. When the conductor 2 is wound, the windings eventually come into contact with each other. However, as shown in FIG. 5B, since the thickness of the conductor 2 on the outer circumference side of the coil 1 is made smaller than its thickness on the inner circumference side by winding the conductor 2, an air-core coil can be made by winding the conductor 2 while preventing the coating on the conductor 2 from being peeled off or damaged.

If the coil 1 in which the coating of the conductor 2 has peeled off or suffered damage, were to be embedded within the green body 10, the inductance value of coil-embedded dust core would lower remarkably.

Figure 5C:
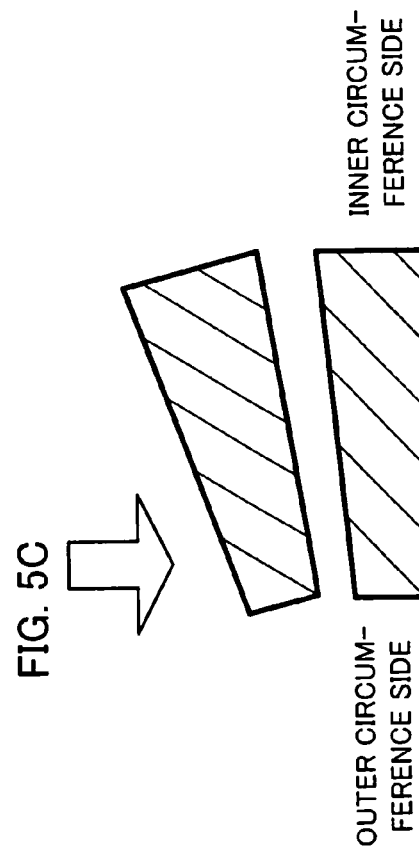

Also, when press processing is rendered in a state in which the flat conductor 2 is wound into a coil and the thickness of the conductor 2 on the outer circumference side of the coil 1 is smaller than its thickness on the inner circumference side as shown in FIG. 5C, the outer circumference side of the coil 1 becomes less prone to damage to the insulation coating. If press processing is rendered in a state in which the thickness of the conductor 2 on the outer circumference side of the coil 1 and the thickness thereof on the inner circumference side are substantially equal as shown in FIG. 5D, the insulation coating on the outer circumference side of the coil 1 is more prone to damage.

Based on the cross-sectional shape of the coil 1 formed after the conductor 2 is wound into a coil, the cross-sectional shape of the conductor 2 may be selected to be trapezoidal or the like when appropriate.

Next, a method for manufacturing the coil 1 in accordance with this embodiment will be described with reference to FIGS. 6 to 10.

Figure 6:
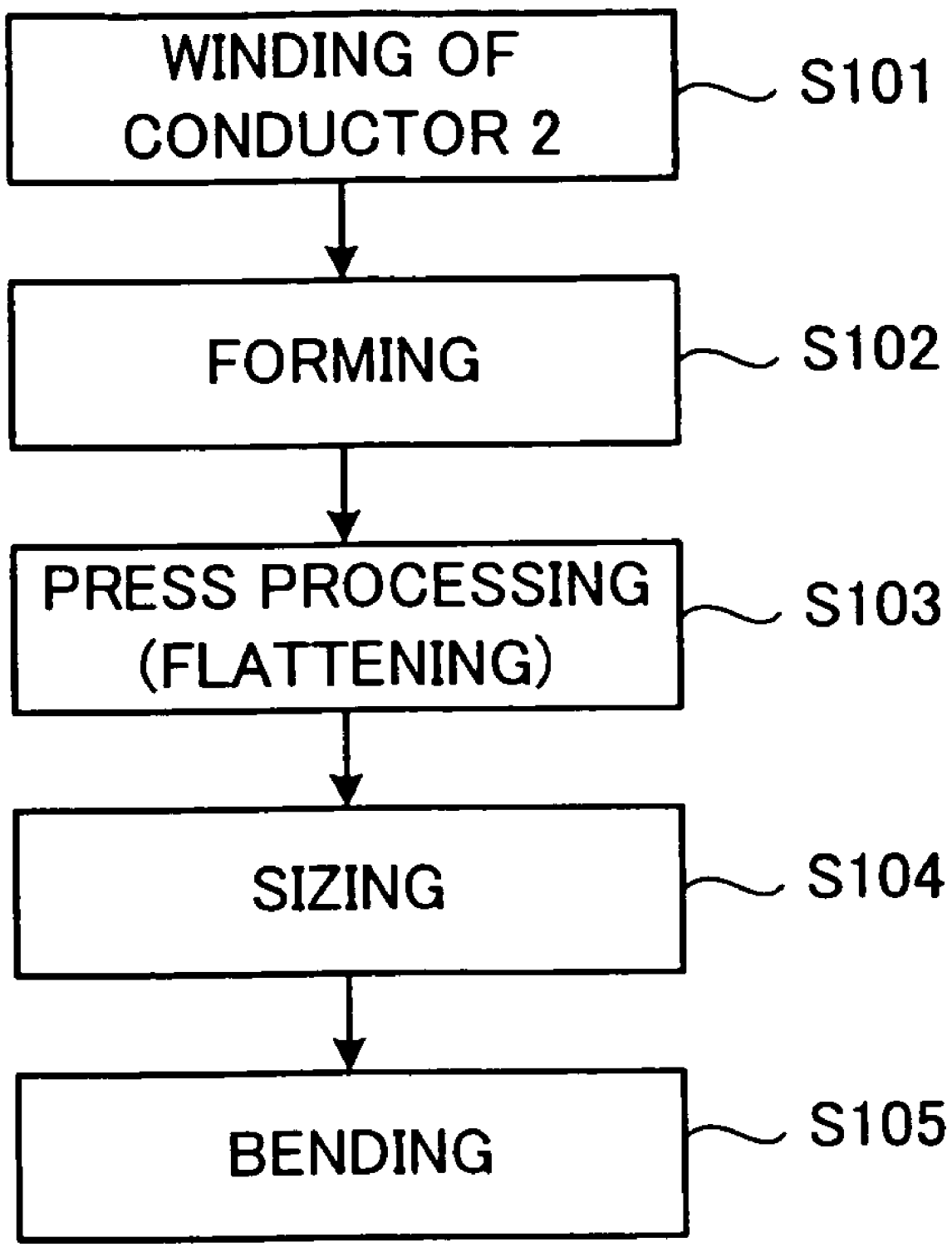
FIG. 6 is a flowchart of a manufacturing process for a coil in accordance with an embodiment.

FIG. 6 is a flowchart showing a process for manufacturing the coil 1 in accordance with this embodiment. As shown in FIG. 6, in the process for manufacturing the coil 1 in accordance with this embodiment, a winding step of the conductor 2 (step S101), a forming step (step S102), a press processing (flattening) step (step S103), a sizing process step (step S104), and a bending step (step S105) are included.

<Winding Step of Conductor 2>

Figure 7A:
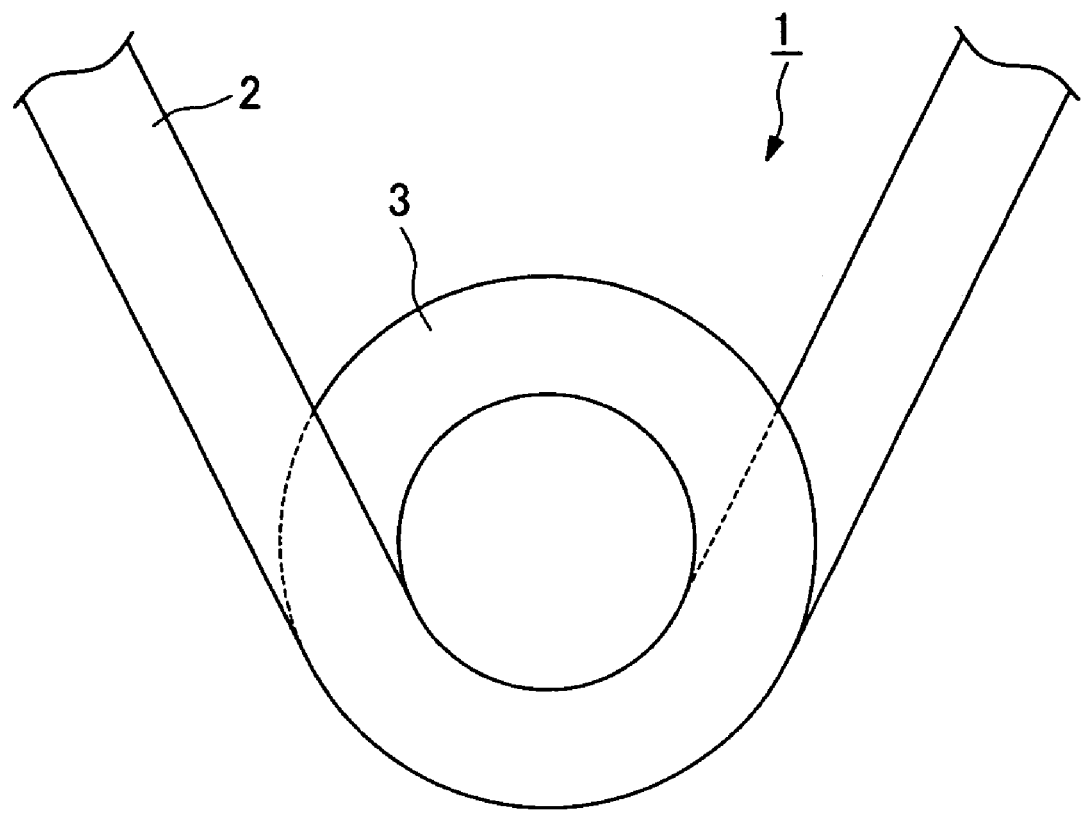
FIGS. 7A and 7B are views for illustrating a winding step.
Figure 7B:
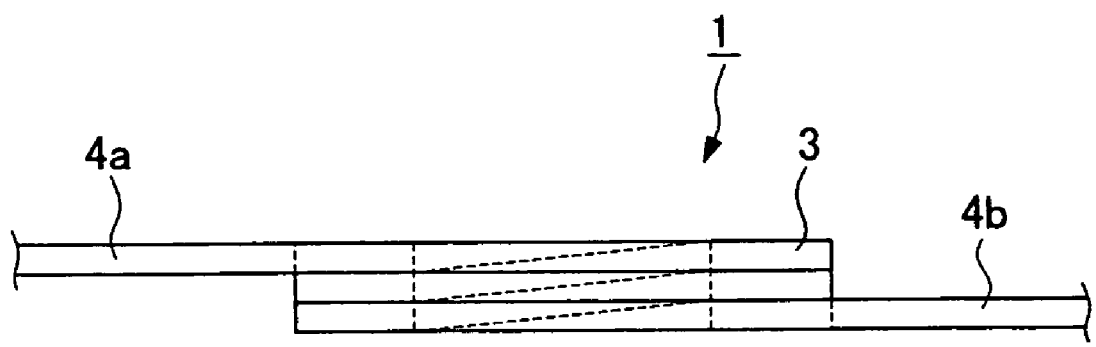

First, in step S101, as shown in FIGS. 7A and 7B, the flat conductor 2 is wound to form the winding section 3 and the lead-out end sections 4a and 4b of the coil 1. The number of turns of the conductor 2 is set appropriately according to the required inductance value, and it can be 1 to 6 turns, preferably 2 to 4 turns. FIG. 7B is a side view of the coil 1 after being wound 2.5 turns in edgewise winding. It is preferable from the viewpoint of decreased number of work processes and improved wire occupation rate that the layers of winding that makes up the coil 1 be brought into very close contact with each other in advance at the stage of winding step in step S101 as shown in FIG. 7B.

<Forming Step>

In the succeeding step S102, forming of the coil 1 is performed. FIG. 8 is a plan view showing a state in which the lead-out end sections 4a and 4b of the conductor 2 are extended from the winding section 3 of the coil 1 by inverse forming. The direction, in which the lead-out end section 4a is extended, is preferably a direction different from the direction in which the lead-out end section 4b is extended. The reason for this is that if the lead-out end sections 4a and 4b are extended in the same direction, it is difficult to form the terminal sections 100 on both sides of the coil-embedded dust core; inconvenience is caused when the lead-out end sections 4a and 4b are subjected to press processing (the details of press processing is described later); and it is difficult to arrange the coil 1 in the center of the green body 10 when the coil-embedded dust core is manufactured. Also, as shown in FIG. 8, forming is preferably performed so that the lead-out end sections 4a and 4b are arranged symmetrically. By doing this, when the coil-embedded dust core using the coil 1 is used as a surface mounting part, the extending directions of the lead-out end sections 4a and 4b, which function as the terminal section 100, can be made symmetrical. Therefore, when the coil 1 is handled, for example, when the coil 1 is placed in a die machine, the direction of the coil 1 need not be distinguished.

<Press Processing (Flattening by Pressing) Step>

After the forming of the coil 1 has been performed in step S102, the process proceeds to step S103. In step S103, the lead-out end sections 4a and 4b are subjected to press processing (flattening by pressing; hereinafter referred to as "flattening".) This step is accomplished to cause the lead-out end sections 4a and 4b of the coil 1 to function as the terminal section 100. Through this step, the plain surfaces of the lead-out end sections 4a and 4b are formed so as to be wider and thinner than the plain surface of the conductor 2.

The press processing in step S103 is preferably performed so that the thickness of the conductor 2 is about 0.1 to 0.3 mm. As described above, the press processing is performed to form the plain surfaces of the lead-out end sections 4a and 4b so as to be wider and thinner than the plain surface of the conductor 2. In addition, however, an effect that the strength of the lead-out end sections 4a and 4b functioning as the terminal section 100 is increased by the press processing can be anticipated.

Figure 9A:
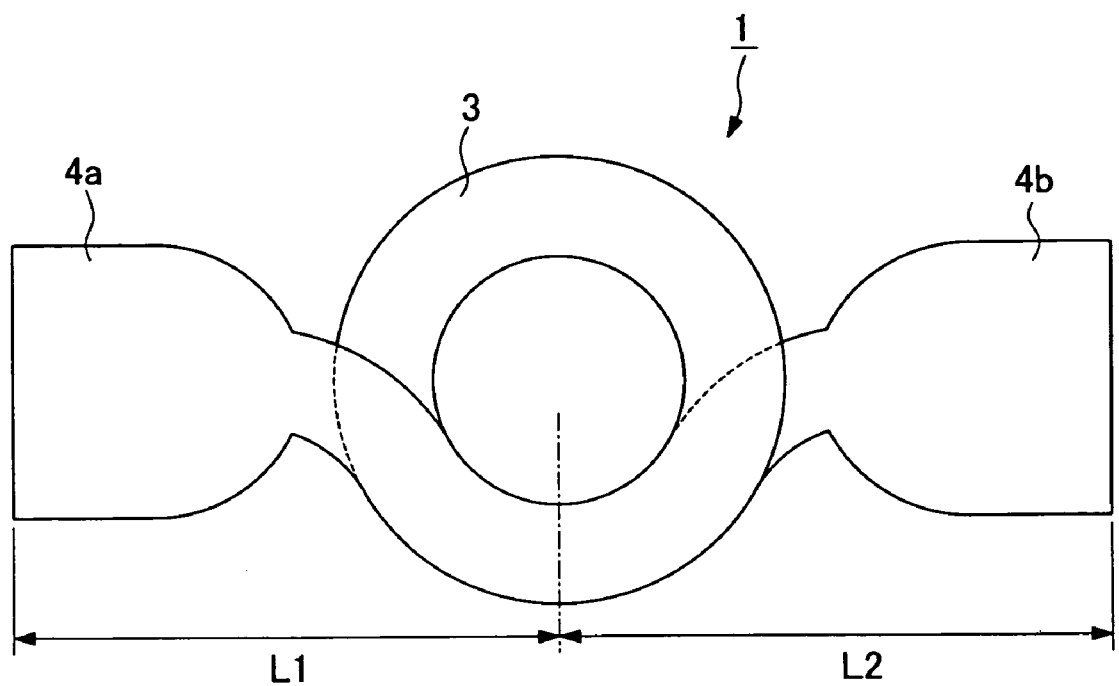
FIGS. 9A and 9B are views for illustrating a press processing step.
Figure 9B:
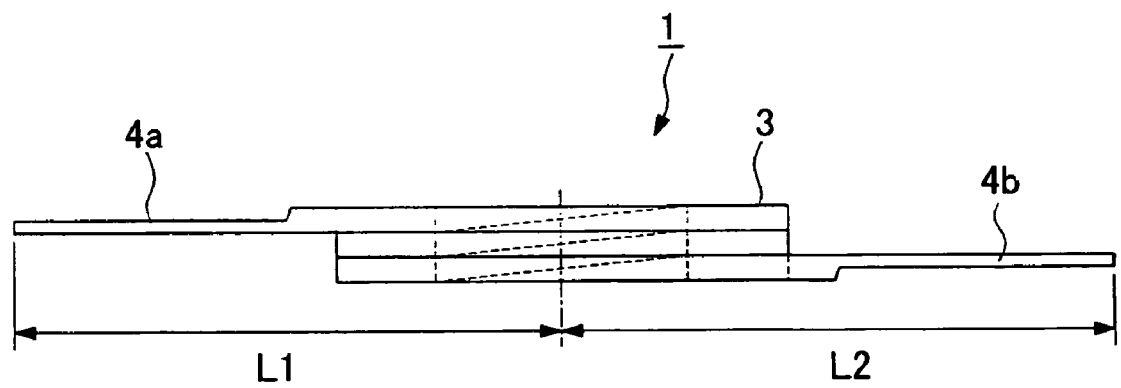

FIG. 9 shows a state after the lead-out end sections 4a and 4b have been subjected to press processing. FIG. 9A is a plan view of the coil 1, and FIG. 9B is a side view of the coil 1.

As shown in FIG. 9A, when the lead-out end section 4a, 4b is subjected to press processing, the conductor 2 in this section elongates in an isotropic manner. Namely, the shapes of the lead-out end sections 4a and 4b cannot be made rectangular by simply pressing the conductor 2. Meanwhile, the shape of the lead-out end sections 4a and 4b is preferably rectangular so as to fit to the land pattern of a substrate on which the coil-embedded dust core using the coil 1 is mounted. This is because the land pattern tends to be small following the improvement in surface mounting density, and it is necessary to improve precision of size and shape of terminals.

<Sizing Process Step>

After the lead-out end sections 4a and 4b have been subjected to press processing in step S103, the process proceeds to step S104. In step S104, the press processed lead-out end sections 4a and 4b are subjected to sizing process. The sizing may be performed by using a cutting die, for example. As described above, since the land pattern of substrate on which the coil-embedded dust core is mounted usually has a rectangular shape, the lead-out end sections 4a and 4b preferably have a rectangular shape to fit to the land pattern. For instance, when using the coil-embedded dust core in a notebook computer, the shape of the lead-out end section 4a, 4b may preferably be rectangular with dimensions of approximately 20×30 mm to 50×60 mm.

It is not a necessary requirement in making the lead-out end sections 4a and 4b function as the terminal sections to make the lead-out end sections 4a and 4b rectangular, and if the size of the lead-out end sections 4a and 4b after the pressing processing is within the land pattern of the substrate, it is possible to omit the sizing process in step S104 appropriately. Although the rectangular shape of the lead-out end section 4a, 4b is not an essential requirement for making the lead-out end section 4a, 4b function as the terminal section 100 as described above, It should be noted that the requirement for the shape and dimensional accuracy of the terminal section 100 is strong nowadays because of small and narrow land pattern caused by the increase in surface mounting density. Therefore, the press processed lead-out end sections 4a and 4b are preferably subjected to sizing process. Now, the coil 1 having been subjected to sizing process has a planar shape, for example, as shown in the plan view of FIG. 3.

<Bending Step>

After the lead-out end sections 4a and 4b have been subjected to sizing process in step S104, the process proceeds to step S105. In step S105, the sizing processed lead-out end sections 4a and 4b are subjected to bending process. This bending step is characteristic of the present invention. This step is performed to arrange the lead-out end sections 4a and 4b functioning as the terminal section 100 on the same plane.

Next, the details of the bending step are explained with reference to FIG. 10. FIGS. 10A to 10C are side views of the coil 1.

Figure 10A:
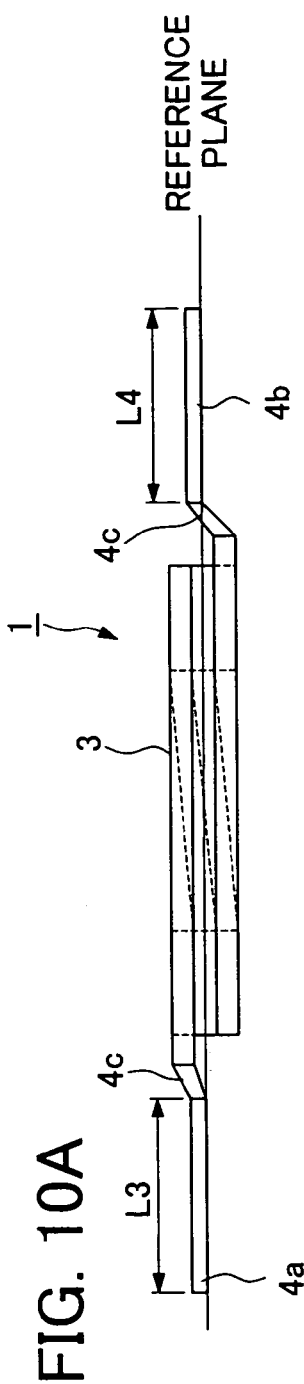
FIGS. 10A to 10C are views for illustrating a bending step.

FIG. 10A is a side view showing a state in which the lead-out end sections 4a and 4b are arranged on the same plane with an intermediate layer of the winding section 3 being a reference plane. As shown in FIG. 10A, when the intermediate layer of the winding section 3 is made a reference plane, the lead-out end sections 4a and 4b are bent at an angle by the substantially same amount, and bent sections 4c are formed between the lead-out end section 4a and the winding section 3 and between the lead-out end section 4b and the winding section 3. When the lead-out end sections 4a and 4b are arranged on the same plane with the intermediate layer of the winding section 3 being a reference plane in this manner, in the above-described sizing process step (step S104), the lengths of the lead-out end sections 4a and 4b are made approximately equal, that is, as shown in FIGS. 9A and 9B, a length L1 from the centerline of the winding section 3 of the coil 1 to the tip end of the lead-out end section 4a is caused to coincide with a length L2 from the centerline of the winding section 3 of the coil 1 to the tip end of the lead-out end sections 4b. Thereby, when the bent sections 4c are formed between the lead-out end section 4a and the winding section 3 and between the lead-out end section 4b and the winding section 3, a length L3 of the lead-out end section 4a can be caused to substantially coincide with a length L4 of the lead-out end sections 4b.

Figure 10B:
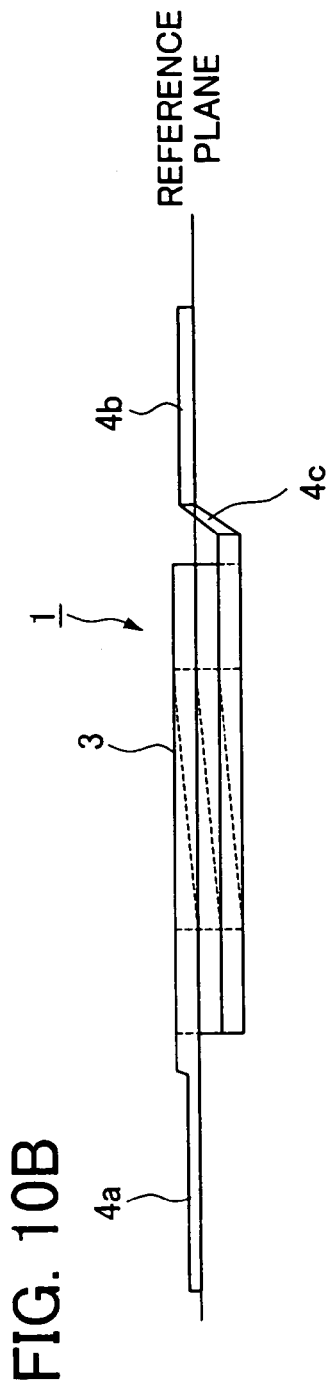

FIG. 10B is a side view showing a state in which the lead-out end sections 4a and 4b are formed on the same plane with the uppermost layer of the winding section 3 being a reference plane, that is, they are formed so that either one of the front and back surfaces of the lead-out end section 4a and either one of the front and back surfaces of the lead-out end section 4b are formed so as to be on the same plane. As shown in FIG. 10B, when the uppermost layer of the winding section 3 is used as a reference plane, only one lead-out end section 4b is bent at an angle, by which the bent section 4c is formed between the lead-out end section 4b and the winding section 3. Also, when the lead-out end sections 4a and 4b are arranged on the same plane with the lowermost layer of the winding 3 being a reference plane, as shown in FIG. 10C, only one lead-out end section 4a may be bent at an angle to form the bent section 4c between the lead-out end section 4a and the winding section 3.

When the lead-out end sections 4a and 4b are arranged on the same plane with the uppermost layer of the winding 3 being a reference plane as shown in FIG. 10B, in the above-described sizing process step (step S104), the length of the lead-out end section 4b is made longer than the length of the lead-out end section 4a. That is, the above-described process of step S101 through step S104 is performed so that the length L2 from the centerline of the winding section 3 of the coil 1 to the tip end of the lead-out end section 4b is longer than the length L1 from the centerline of the winding section 3 of the coil 1 to the tip end of the lead-out end section 4a. The same is true for the case where the lead-out end sections 4a and 4b are arranged on the same plane with the lowermost layer of the winding 3 being a reference plane.

When the bent section 4c is formed by bending the lead-out end section 4a, 4b, a portion subjected to flattening may be bent, or a portion not subjected to flattening may be bent. Since the thickness of the lead-out end section 4a, 4b is 0.1 to 1.0 mm before press processing and 0.1 to 0.3 mm after press processing, the lead-out end sections 4a and 4b can be bent easily.

The bending step (step S105), which is the step characteristic of the present invention, has been described above with reference to FIG. 10. This step is essential in arranging the lead-out end sections 4a and 4b on the same plane. That is, in a state in which the bent section 4c is not formed in both portions between the lead-out end section 4a and the winding section 3 and between the lead-out end section 4b and the winding section 3 as shown in FIGS. 7B and 9B, the lead-out end sections 4a and 4b cannot be arranged on the same plane.

In the above-described embodiment, an example in which the bending step (step S105) is performed after the press processing step (step S103) and the sizing process step (step S104) has been explained. However, the press processing step (step S103) and the sizing process step (step S104) may be performed after the bending step (step S105) has been performed. Also, the bending step (step S105) may be performed between the press processing step (step S103) and the sizing process step (step S104).

Figure 10C:
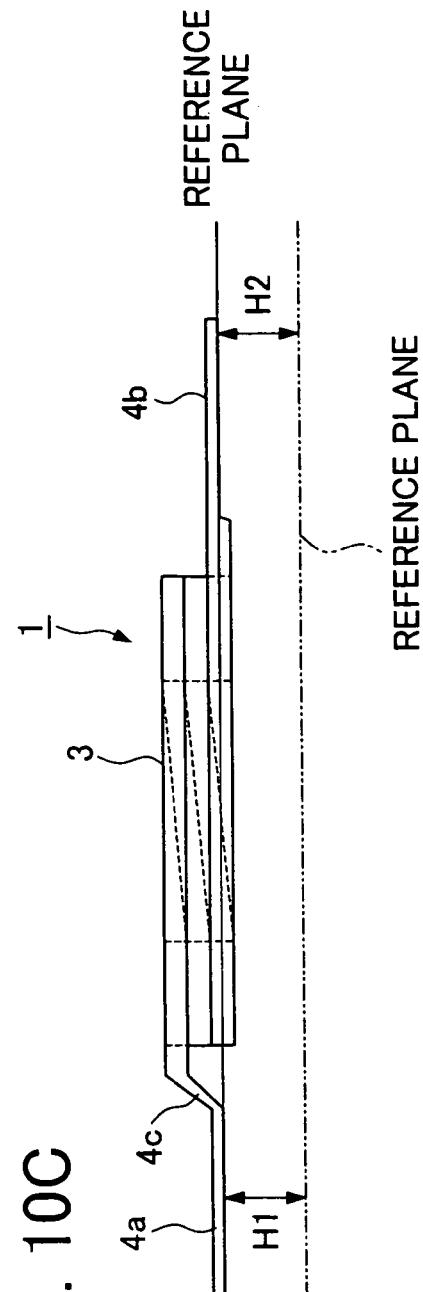

Although described later in detail, when the coil 1 in which the lead-out end sections 4a and 4b are arranged on the same plane as shown in FIGS. 10A to 10C is used, an effect that a desired inductance value can be obtained and variations in inductance value can be reduced, is achieved. It is a matter of course that the reference plane is not limited to ones indicated by a solid line in FIGS. 10A to 10C, and a reference plane indicated by an imaginary line in FIG. 10C can be used. In this case, the bent section 4c may be formed so that a distance H1 from the predetermined reference plane to the lead-out end section 4a (either one of the front and back surfaces thereof) is approximately equal to a distance H2 from the predetermined reference plane to the lead-out end section 4b (either one of the front and back surfaces thereof).

Although the method in which the coil 1 is manufactured by performing the steps of step S101 through step S105 has been described above, the press processing step (step S103) and the sizing process step (step S104) can be performed substantially at the same time. This case where these two steps are performed substantially at the same time includes both a case where the sizing process is performed in a state in which the lead-out end section 4a, 4b functioning as the terminal section 100 is subjected to a predetermined pressing force and a case where the sizing process is performed immediately after the lead-out end section 4a, 4b functioning as the terminal section 100 is subjected to a predetermined pressing force. In order to perform the press processing step (step S103) and the sizing process step (step S104) substantially at the same time, for example, the configuration may be such that a cutting die is provided around a punch for press processing, and the cutting die is lowered in the state in which the lead-out end section 4a, 4b is subjected to the predetermined pressing force or immediately after the lead-out end section 4a, 4b is subjected to the predetermined pressing force to cut the lead-out end section 4a, 4b into a predetermined shape.

Further, the press processing step (step S103), the sizing process step (step S104), and the bending step (step S105) can be performed substantially at the same time. That is to say, the coil 1 in the state shown in FIG. 4 can be obtained from the state of coil 1 shown in FIG. 8 by one step. In this case, the bent section 4c may be formed in at least one portion between the lead-out end section 4a and the winding section 3 or between the lead-out end section 4b and the winding section 3 by bending a part of the lead-out end section 4a, 4b while applying the predetermined pressing force to the lead-out end section 4a, 4b. Immediately after the bent section 4c has been formed, for example, a cutting die is lowered to cut the lead-out end section 4a, 4b into a predetermined shape.

Since, as described above, the coil 1 is formed so that the lead-out end sections 4a and 4b function as the terminal section 100, an independent terminal section need not be provided. That is to say, according to the coil-embedded dust core in accordance with this embodiment, a connection part between the coil and the terminal section is eliminated. The elimination of connection part avoids the conventional problems such as joint failure between the coil and the terminal section and insulation failure of the coil and terminal section with respect to the magnetic powder. Also, since the coil 1 in accordance with this embodiment is an air-core coil that is made by winding a flat conductor 2, high inductance value can be provided with a small number of turns, and downsizing (low in height) of core can further be promoted. Further, when the press processing and the sizing process are performed substantially at the same time, the number of processes for making the coil 1 can be decreased, so that the work efficiency is improved. Moreover, when the press processing and the sizing process are performed substantially at the same time, the coil 1 need not be moved, so that the positioning accuracy at the time of sizing process becomes higher than before, by which an increase in the working accuracy of the lead-out end sections 4a and 4b that function as the terminal section 100 can be anticipated. Still further, for the coil 1 in which the lead-out end sections 4a and 4b are arranged on the same plane, the inductance value varies less, and the performance is high.

Next, a method for manufacturing the coil-embedded dust core in accordance with this embodiment will be described with reference to FIGS. 11 to 15.

Figure 11:
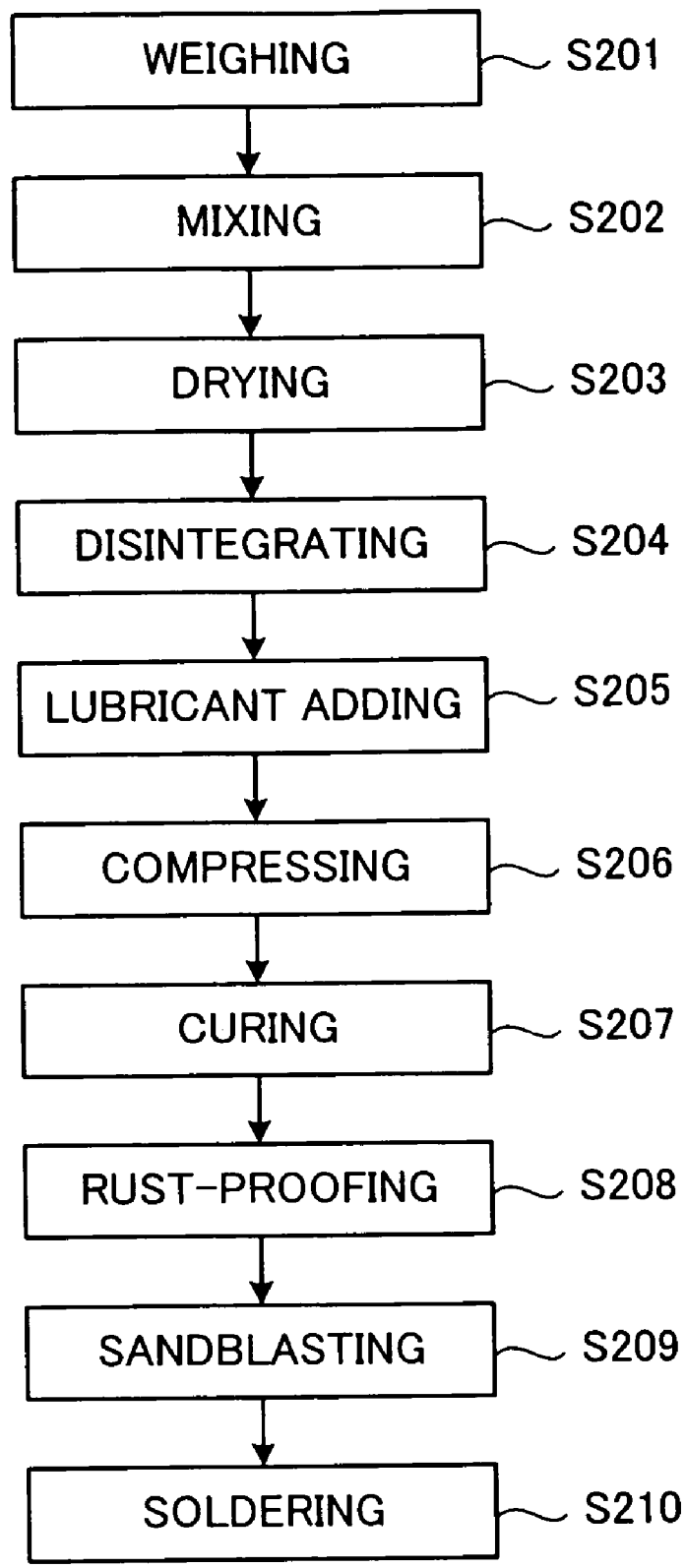
FIG. 11 is a flowchart of a manufacturing process for a coil-embedded dust core in accordance with an embodiment.

FIG. 11 is a flowchart showing a process for manufacturing the coil-embedded dust core in accordance with the present invention. The coil 1 that is formed by winding the flat conductor 2 is manufactured in advance.

First, a ferromagnetic metal powder and an insulating material are selected according to the required magnetic properties, and they are weighed respectively (step S201). If a cross-linking agent is added, the cross-linking agent is also weighed in step S201.

After weighing out the ferromagnetic metal powder and the insulating material, they are mixed (step S202). When the cross-liking agent is added, the ferromagnetic metal powder, the insulating material, and the cross-linking agent are mixed in step S202. The mixing is performed by using a pressure kneader and preferably at room temperature for 20 to 60 minutes. The resultant mixture is dried preferably at a temperature of about 100 to 300° C. for 20 to 60 minutes (step S203). Next, the dried mixture is disintegrated to obtain ferromagnetic powder for dust core (step S204).

In the succeeding step S205, a lubricant is added to the ferromagnetic powder for dust core. After the lubricant is added, the powder and lubricant are preferably mixed for 10 to 40 minutes.

Figure 12:
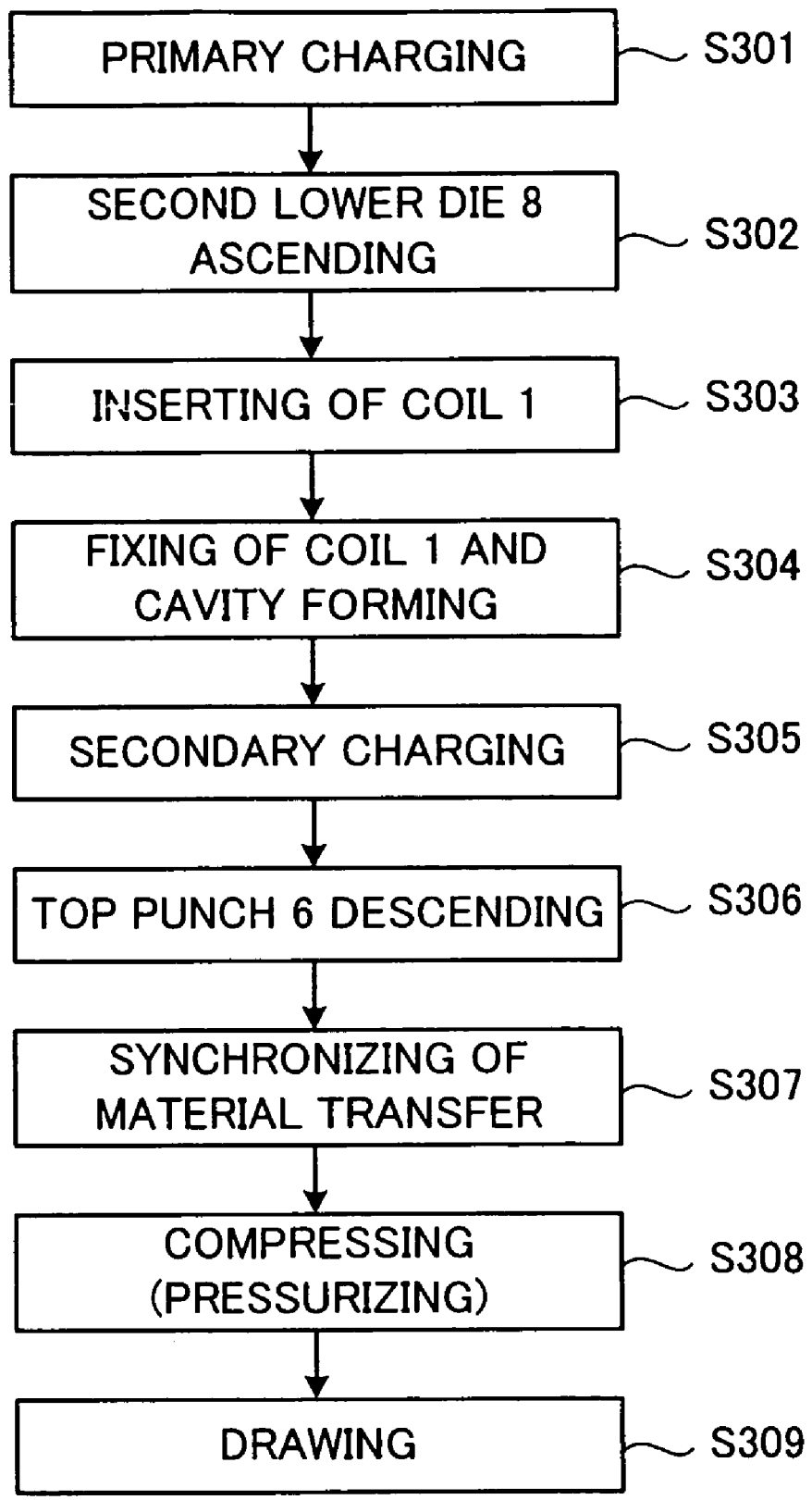
FIG. 12 is a flowchart illustrating each step of a compressing step in step S206 in FIG. 11.

After the lubricant is added, a compressing step (step S206) is conducted. The compressing step in step S206 is described below with reference to FIGS. 12 to 15. FIG. 12 is a flowchart illustrating each step of a compressing step. FIGS. 13 to 15 show a state in which the ferromagnetic powder for dust core, which the lubricant has been added to and mixed with, is compacted by using a die machine.

First, the die machine preferably used in the compressing process of this embodiment will be explained with use of FIG. 13A.

As shown in FIG. 13A, the die machine is constituted by an upper die 5A and a first lower die 5B, a top punch 6 and a bottom punch 7 and a second lower die 8. The upper die 5A and the first lower die 5B, and the top punch 6 and the bottom punch 7 are provided at the positions at which they oppose each other, the upper die 5A and the top punch 6 ascending and descending in the upper die 5A constitute an upper die set, and the first lower die 5B and the bottom punch 7 ascending and descending in the first lower die 5B and a second lower die 8 constitute a lower die set. The bottom punch 7 is divided into a bottom punch main 7a and a cylindrical divided body (a tubular member) 7b having a top part in substantially the same shape as the planar shape of the coil 1, and the cylindrical divided body 7b moves ascendably and descendably in the first lower die 5B. The cylindrical divided body 7b is included in the bottom punch 7 to equalize the compacted body densities of the part corresponding to the winding section 3 of the coil 1 and the other parts that are not corresponding to the winding section 3 of the coil 1. Namely, this is the idea for charging a smaller amount of ferromagnetic powder for dust core to the part corresponding to the winding section 3 of the coil 1 than to the other parts that are not corresponding to the winding section 3 of the coil 1.

Meanwhile, the reason why a cylindrical divided body corresponding to the cylindrical divided body 7b is not provided in the top punch 6 is as follows. Namely, when ferromagnetic powder for the dust core is charged in the cavity of the die machine in this embodiment, charging by leveling off the powder with use of a feeder box is performed. Correspondingly to this, it is most desired to perform upward pressurization with use of a punch having a flat surface. Since the bottom punch 7 is divided to take measures to make the compacted body density uniform, it is not necessary to divide the top punch 6. It is not preferable to divide the top punch 6 from the viewpoint of the cost, and in addition, even if the top punch 6 is divided, compressing cannot be performed with the procedure that will be described later.

Before a compressing process (step S206) is started, the die machine is in the state shown in FIG. 13A. As will be explained hereinafter, the upper die 5A, the first lower die 5B, the top punch 6, the cylindrical divided body 7b and the second lower die 8 changes their positions from the state shown in FIG. 13A in each step, but the bottom punch main 7a is not moved from a predetermined reference plane in any steps. Relative movement of the upper die 5A, the first lower die 5B, the top punch 6, the cylindrical divided body 7b and the second lower die 8 in the compressing process (step S206) will be explained hereinafter, with the upper surface of the bottom punch main 7a as the reference plane (hereinafter, called "reference plane").

(Step S301 Primary Charging)

The first lower die 5B, the cylindrical divided body 7b and the second lower die 8 ascend to a predetermined position from the state in FIG. 13A, namely the reference plane at the same time to form a cavity inside the first lower die 5B (FIG. 13B). Here, as shown in FIG. 13B, the upper surfaces of the first lower die 5B and the second lower die 8 are located on the same plane, respectively. Since the bottom punch main 7a does not move, and only the cylindrical divided body 7b ascends, the bottom punch main 7a and the cylindrical divided body 7b are located at different levels from each other.

When positioning of the cylindrical divided body 7b and the first lower die 5B is completed, a feeder box F housing a mixed powder 20 (mixture of the above-described insulation-coated ferromagnetic powder for dust core with a lubricant) is moved on the first lower die 5B, and charges a predetermined amount of mixed powder 20 into the cavity of the first lower die 5B. Since the feeder box F performs charging by leveling, the primary charging amount and the volumetric capacity of the cavity of the first lower die 5B become substantially the same. Consequently, it is necessary to control the positions of the cylindrical divided body 7b and the first lower die 5B previously and accurately based on the thickness of the coil-embedded dust core which is desired to be finally obtained and the number of windings of the coil 1.

When the mixed powder 20 is charged by leveling into the cavity of the first lower die 5B by the feeder box F, the feeder box F is temporarily retreated.

(Step S302 Rise of the Die 8)

Subsequently, the second lower die 8 accurately ascends to the predetermined position as shown in FIG. 13C. In concrete, the second lower die 8 ascends so that an upper surface of a notched part 8a of the second lower die 8 is located on the same plane as the upper surface of the first lower die 5B. The second lower die 8 ascends in step S302, but the first lower die 5B and the cylindrical divided body 7b remain at the same position as that shown in FIG. 13B.

(Step S303 Insertion of the Coil 1)

Figure 14A:
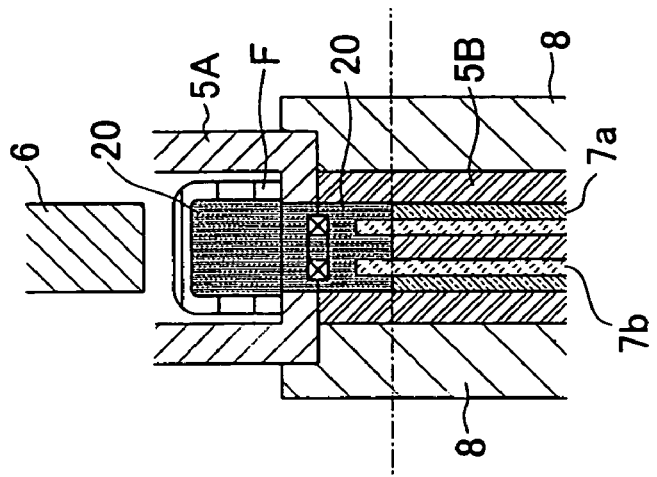
FIGS. 14A to 14C are views explaining the compressing step in step S206 in FIG. 11.

Next, as shown in FIG. 14A, the coil 1 with the flat conductor 2 being wounded around is inserted into the first lower die 5B. The coil 1 is an air-core coil previously. produced according to the aforementioned procedure. Engraving (groove) is formed on the upper surface of the first lower die 5B to fit to the shapes of the lead-out end sections 4a and 4b. In step S303, the coil 1 is placed inside the first lower die 5B so that the lead-out end sections 4a and 4b are inserted into the engraving. The lead-out end sections 4a and 4b are formed on the same plane as shown in FIG. 10, and therefore when the lead-out end sections 4a and 4b are inserted to fit in the engraving of the first lower die 5B, for example, the coil 1 is horizontally positioned inside the first lower die 5B without being obliquely positioned. Namely, the coil 1 is ultimately positioned horizontally at the center of the green body 10 with the horizontal direction as the reference, (Step S304 Fixing of the Coil 1 and Cavity Formation)

Figure 14B:
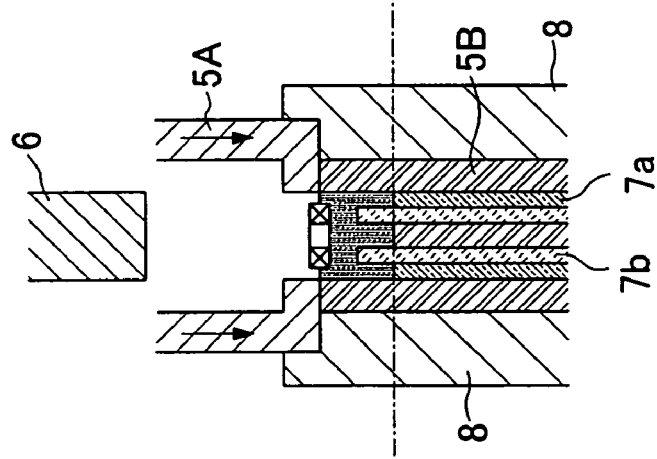

After the coil 1 is inserted into the first lower die 5B in Step S303, the upper die 5A descends to the first lower die 5B as shown in FIG. 14B. By the descending of the upper die 5A, the lead-out end sections 4a and 4b of the coil 1 are sandwiched by the upper die 5A and the first lower die 5B to be fixed. Consequently, the movement of the coil 1 in a lateral direction is controlled. As shown in FIG. 14B, following the descending of the upper die 5A, a new cavity by the upper die 5A is formed on the upper surface of the coil 1.

(Step S305 Secondary Charging)

Figure 14C:
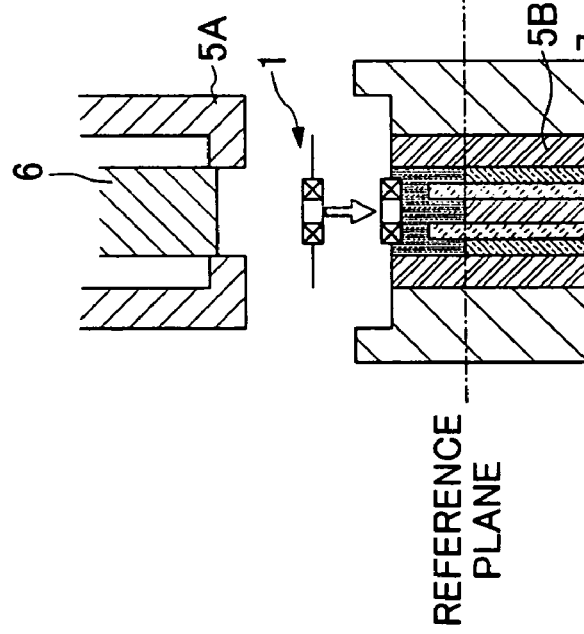

When the descending of the upper die 5A is detected by a sensor not shown, the temporarily retreated feeder box F approaches the die machine again. As shown in FIG. 14C, a predetermined amount of the mixed powder 20 is charged inside the cavity that is newly formed in step S304 so as to cover the upper surface of the coil 1. As for the secondary charging, charging by leveling up to the upper surface of the bottom part of the upper die 5A is performed as in the primary charging. Relative position control of the first lower die 5B, the cylindrical divided body 7b and the bottom punch main body 7a in a compacting direction is previously performed in the aforementioned FIG. 13B so that the coil 1 be accurately positioned at the center in the axial direction of the green body 10.

(Step S306 Lowering of the Top Punch 6)

When the charging is finished in FIG. 14C, the feeder box F is retreated again, and at the same time, the top punch 6 descends to the upper surface of the bottom part of the upper die 5A as shown in FIG. 15A. Namely, in this state, a tip end of the top punch 6 and the upper surface of the bottom part of the upper die 5A are located on the same plane.

(Step S307 Synchronism of Material Transfer, Step S308 Pressurization)

At substantially the same time when the top punch 6 descends in step S306 and the tip end of the top punch 6 and the upper surface of the bottom part of the upper die 5A are located on the same plane (FIG. 15A), the upper die 5A, the first lower die 5B, the second lower die 8 and the cylindrical divided body 7b descend in synchronism with the top punch 6 (FIG. 15B). As a result, the mixed powder 20 sandwiched by the top punch 6 and the bottom punch 7 is pressurized in the vertical direction and compressed in the axial direction of the coil 1 (FIG. 15C). Here, as described above, the lead-out end sections 4a and 4b of the coil 1 are sandwiched by the upper die 5A and the first lower die 5B and fixed. Consequently, the upper die 5A and the first lower die 5B gradually descend according to the compression amount in the axial direction while holding the lead-out end sections 4a and 4b of the coil 1 so that the lead-out end sections 4a and 4b are not broken (FIG. 15B, FIG. 15C). As shown in FIG. 15B, the cylindrical divided body 7b also gradually descends based on the lowering amount of the top punch 6, namely, the compression amount in the axial direction. Then, the cylindrical divided body 7b ultimately descends to the reference plane and stops (FIG. 15C). The condition of pressurization in FIG. 15B and FIG. 15C is desired to be 100 MPa to 600 MPa.

The mixed powder 20 charged in the part corresponding to the winding section 3 of the coil 1 is compacted more easily than the mixed powder 20 charged in the part which is not corresponding to the winding section 3, and therefore, if the same amount of the mixed powder 20 is charged into each of the part corresponding to the winding section 3 of the coil 1 and the parts which are not corresponding to the winding section 3, the density of the green body 10 cannot be ultimately made uniform entirely. Attention is being paid to this, the cylindrical divided body 7b is formed into substantially the same shape as the plane shape of the coil 1 and charging is performed so that a smaller amount of the mixed powder 20 is charged into the part corresponding to the winding section 3 than to the parts which are not corresponding to the winding section 3. As a result, it becomes possible to equalize the density and the compression ratio of the part corresponding to the winding section 3 of the coil 1 and the parts which are not corresponding to the winding section 3, that are in concrete, the parts corresponding to the hollow part of the coil 1, the surroundings of the lead-out end sections 4a and 4b of the coil 1, and the corner parts of the dust core 10.

Step S306 to step S308 are performed in succession, and the components of the die other than the bottom punch main 7a, namely, the upper die 5A, the top punch 6, the first lower die 5B, the second lower die 8 and the cylindrical divided body 7b descend to predetermined positions, respectively in steps S307 and S308.

(Step S309 Drawing)

After compression-forming in FIG. 15C, the upper die 5A and the top punch 6 ascend as in FIG. 15D, and the first lower die 5B and the second lower die 8 descend to the reference plane. Then, the compacted body (coil-embedded dust core) is drawn out of the die, whereby one cycle of compressing step is finished. On the occasion of drawing in step S309, the first lower die 5B, the second lower die 8, the bottom punch main body 7a and the cylindrical divided body 7b are positioned on the reference plane. Since the upper die 5A and the top punch 6 also ascend to the original position, in FIG. 15D, the die machine is returned to the state shown in FIG. 13A. A ring-shaped trace corresponding to the shape of the top part of the cylindrical divided body 7b remains on the compacted body which is obtained through the aforementioned compressing step (step S206).

As a result of undergoing the steps shown in the above steps shown in step S301 to step S309, a small-sized compacted body (coil-embedded dust core) of about 5 mm to 15 mm long, 5 mm to 15 mm wide, and 2 mm to 7 mm thick can be obtained. According to the manufacturing method of the coil-embedded dust core of the present invention, performing is not required, and only one compressing forming is sufficient. Accordingly, the present invention is excellent in working efficiency and productivity. The structure of the die machine is devised, the cylindrical divided body 7b is formed into substantially the same shape as the plane shape of the coil 1, charging is performed so that a smaller amount of the mixed powder 20 is charged to the part corresponding to the winding section 3 than to the parts which are not corresponding to the winding section 3, and thereafter pressurization is performed. As a result, the density of the compacted body can be made uniform.

By accurately controlling the position of the compacting direction with use of the method for manufacturing the coil-embedded dust core of the present invention, the position in the axial direction of the coil 1 can be accurately positioned at the center of the green body 10 as shown in FIG. 2B. As described above, the position of the coil 1 in the compacting direction has a large influence on inductance of the coil-embedded dust core, and accurate positioning of the coil 1 in the axial direction at the center of the green body 10 can provide a large inductance value and reduces variations in inductance value significantly. It is considered that the variation of the inductance value is reduced as described above because the magnetic path length of the coil-embedded dust core and a sectional area can be controlled to be predetermined values by accurately controlling the axial position of the coil 1. When the position in the axial direction of the coil 1 is inclined, magnetic saturation easily occurs locally, and a tendency that the inductance value decreases can be seen, but according to the method for manufacturing the coil-embedded dust core of the present invention, such a problem does not occur and a desired inductance value can be obtained with stability. The operation of the die machine is explained with the upper surface of the bottom punch 7a as the reference plane so far, but the reference plane is not limited to what is described above if only the die machine relatively moves similarly.

After the compressing step in step S206 shown in FIGS. 11 and 12, a curing step (heat treatment step) is conducted (step S207). In the curing step, the compacted body obtained in the compressing step (step S206) is kept at temperatures of 150 to 300° C. for 15 to 45 minutes. By doing this, the resin within the compacted body is hardened.

After the curing step, a rust-proofing step is conducted (step S208). Rust-proofing is done by spray coating epoxy resin, for example, on the compacted body consisting of the coil 1 and the green body 10. The thickness of the coat resulting from the spray coating is approximately 15 μm. After rust-proofing, the compacted body is preferably subjected to heat treatment at 120 to 200° C. for 15 to 45 minutes.

As described above, in the coil-embedded dust core in accordance with this embodiment, a part of the coil 1 is used as the terminal section 100. However, the conductor 2 used in the coil-embedded dust core has an insulation film such as an enamel film formed on the surface thereof to begin with. According to the observation made by the inventors, a copper oxide film is formed directly underneath the insulation film in the curing step in step S207. Further, a paint film is formed on the insulation film through the rust-proofing step (step S208). These films formed on the terminal section 100 are removed in a sandblasting step (step S209).

One way to remove the three layers of films formed on the surface of the coil 1 is to corrode them with chemicals. However, because different chemicals are required to remove different films, several treatments must be rendered in order to remove the three layers of films. In addition, the chemical corrosion method requires heating of the chemicals, which entails a risk of alkaline particles or acidic particles attaching to the paint film or the insulation film of the terminal section 100 when the chemicals are heated. Such attachment would result in progressive corrosion of the paint film or the insulation film over a long period of time, which is likely to cause lowered rust-proofing efficiency or a short circuit between the coil 1 layers. To avoid such a risk, there is available a mechanical removing method using a tool. However, a tool that may damage the copper part of the conductor 2, cannot be used because the thickness of the terminal section 100 of the coil-embedded dust core in accordance with this embodiment is about 5 mm or smaller (about 0.1 to 0.3 mm). Consequently, in this embodiment, a method for removing the three layers of films by sandblasting is used.

When the terminal section 100 is to be surface mounting terminal section, the terminal section 100 is soldered (step S210). Thereafter, it would be convenient to bend the terminal section 100 which has become wide through flattening process, as necessary when mounting the coil-embedded dust core on a substrate. In that case, terminal section 100 is bent along the side of the green body 10.

The following effects may be obtained from the coil-embedded dust core according to this embodiment.

(1) Since the position of the coil 1 in the axial direction is accurately positioned at the center of the green body 10 and the density of the compacted body is uniformed entirely, the variations of the inductance value is significantly reduced, and a predetermined inductance value can be obtained with stability.

(2) Because the coil is formed by winding the flat conductor 2, high inductance can be obtained with a small number of turns. Also, a compact (low in height) coil-embedded dust core measuring 5 to 15 mm long by 5 to 15 mm wide by 2 to 7 mm thick can be obtained.

(3) Because the lead-out end section 4a, 4b, which is a part of the coil 1, is used as the terminal section 100, there is no need for forming a connection part between the coil 1 and the terminal section. Therefore, problems of joint failure and insulation failure caused by the connection part can be solved.

(4) Because the lead-out end sections 4a and 4b are formed on the same plane, positioning can be performed easily and exactly when the coil 1 is arranged in the die machine. Thereby, the mixed powder 20 can be filled uniformly, so that the inductance value varies less.

(5) Because the lead-out end section 4a, 4b, which is a part of the coil 1, is used as the terminal section 100, there is no need for preparing a terminal section separately. Therefore, the number of parts can be decreased.

EXAMPLE

The coil-embedded dust core in accordance with the present invention will be described in detail by using an example.

Example 1

Thirty samples of the coil-embedded dust core having a core size of 12.5 mm long×12.5 mm wide×3.5 mm thick were made according to the following procedure:

The following were prepared:

Magnetic powder: Permalloy powder manufactured through atomizing method (45% Ni—Fe; mean particle size 25 μm)

Insulating material: silicone resin (SR2414LV by Toray Dow Corning Silicone Co., Ltd.) Lubricant: aluminum stearate (5A-1000 by Sakai Chemical Industry)

Next, 2.4 wt % of the insulating material was added to the magnetic powder, and these were mixed for 30 minutes at room temperature using a pressure kneader. Following this, the mixture was exposed to air and dried for 30 minutes at 150° C., thereafter 0.4 wt % of the lubricant was added to the dried magnetic powder and mixed for 15 minutes in a V mixer.

Figure 16A:
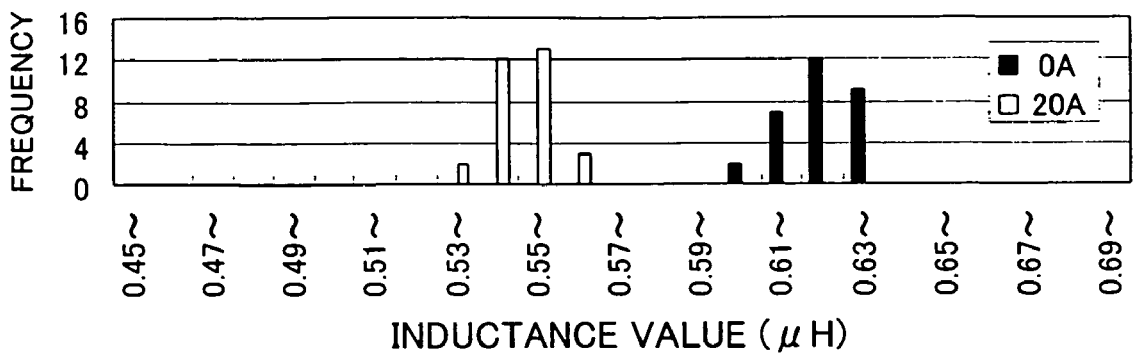
FIG. 16 is a graph showing inductance values measured in example 1, comparison example 1, and comparison example 2.

Subsequently, compressing was performed according to the procedure in FIG. 13A to FIG. 15D, and 30 compacted bodies are made. The coil 1 is formed by winding the inductor 2 with a rectangular section (0.45 mm×2.5 mm) 2.5 turns. Pressure in FIG. 15D is set at 490 MPa. By heat-treating the compacted body after pressurized at 200° C. for 15 minutes, silicone resin as an insulating material is hardened, and the terminal section 100 was bent, whereby thirty samples of the coil-embedded dust cores were made. The inductance values of thirty samples are shown in FIG. 16A. "0A" and "20A" in FIG. 16A show a value of a direct current which is superposed on the inductance measuring AC signal (0.05 V, 100 kHz).

As shown in FIG. 16A, it is understood that the samples according to this embodiment for which compressing is performed according to the procedural steps in FIG. 13A to FIG. 15D have a small variation in inductance value. In concrete, in the case with only an alternate current (in the case in which the superposed direct current is 0A), the inductance values were all within the range of 0.60 to 0.64 μH, and the difference between the minimum value and the maximum value was only 0.04 μH. From FIG. 16A, it is understood that in the case in which the direct current of 20A is superposed, the same tendency as in the case with only the alternate current is also shown. Namely, all the inductance values were in the range of 0.53 μH to 0.57 μH, the difference between the minimum value and the maximum value was only 0.04 μH. Consequently, samples of the present invention which were compressed according to the procedural steps in FIG. 13A to FIG. 15D have a small variation in the inductance value and superior DC bias characteristics.

Next, the density of the center parts of the samples was measured with Gamma Densomat made by Creveserge (a density measuring device using γ rays). As a result, all of the density of the hollow part ① of the coil 1, the density of the part ② corresponding to the lower surface of the winding section ③ of the coil 1, and the density of the part ③ corresponding to the upper surface of the winding section 3 of the coil 1 were 6.4 to 6.5 g/cm. As for the densities of the part ② corresponding to the lower surface of the winding section 3 of the coil 1, and the part ③ corresponding to the upper surface of the winding section 3 of the coil 1 those shown in FIG. 2B, the density of the part with the maximum number of windings, that is, the part with three turns was measured.

When the position in the compacting direction (thickness direction) of the coil 1 was measured from the X-ray projection photograph (made by Shimadzu Corporation), it was recognized that the coil 1 was positioned at the center in the axial direction of the green body 10.

Comparison Example 1

Figure 16B:
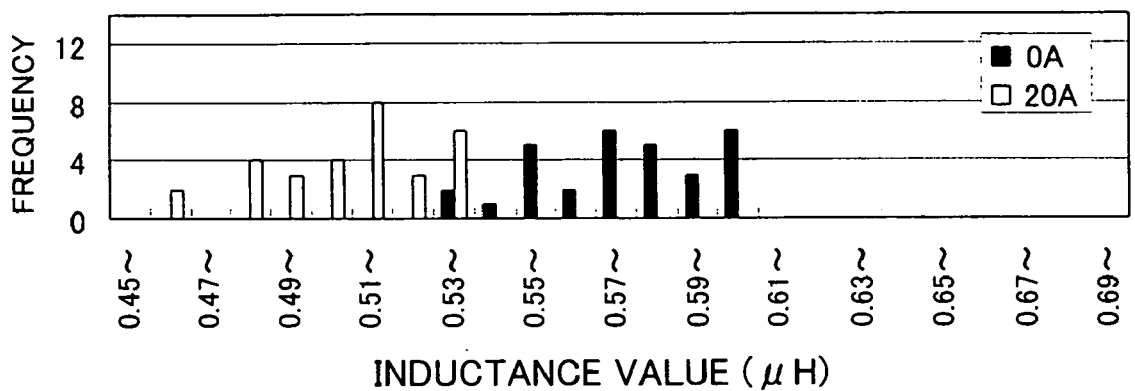

Before the coil 1 is inserted in FIG. 14A, the lower core was preformed. Before main pressurization in FIG. 15D, the bottom punch 7 was replaced with the one having the flat surface, and the main pressurization was performed. With the same procedure as in the example 1 except for this, thirty samples of the coil-embedded dust cores were made. On making these samples, the pressure in the performing was set at 150 MPa, and the main pressurization in FIG. 15D was performed at 490 MPa. The inductance values of the samples in comparison example 1 are shown in FIG. 16B. The measurement condition of the inductance values is the same as in the example 1.

When FIG. 16A and FIG. 16B are compared, it is understood that the samples of which inductance values are shown in FIG. 16B, that is, the samples with the lower cores being preformed have large variations in the inductance values. In concrete, in the case with only an alternate current (in the case in which the superposed direct current was 0A), the inductance values of the samples were all in the range from 0.53 to 0.61 μH, and the difference between the minimum value and the maximum value was 0.08 μH. When the direct current of 20A was superposed, the inductance values of the samples were all in the range of 0.46 to 0.54 μH, and the difference between the minimum value and the maximum value was 0.08 μH.

Next, as a result of measuring the densities of the center parts of the samples in Comparison example 1 as in the example 1, the densities were from 6.6 to 6.8 g/cm³.

When the position of the coil 1 was measured from the X-ray projection photograph (made by Shimadzu Corporation), it was recognized that the position of the coil 1 in the compacting direction (thickness direction) was deviated upward from the center in the axial direction of the green body 10.

From the above result, it was found out that the samples with the lower cores being preformed have little high density at the center parts as compared with the samples of the example 1 for which compression was performed according to the procedural steps in FIG. 13A to FIG. 15D, but have larger variations in the inductance values and smaller inductance values than the samples of the example 1. It is assumed that this is because magnetic saturation occurs locally since the position of the coil 1 is deviated from the center of the green body 10 in the axial direction.

Comparison Example 2

Thirty samples of the coil-embedded dust cores were made by the same procedure as in the example 1 except for the following. points.

In the steps in FIG. 13A to FIG. 15D, compression was performed with the cylindrical divided body 7b being fixed at the reference plane. Namely, the charging amount of the mixed powder 20 was not adjusted for the part corresponding to the winding section 3 of the coil 1 and the parts which are not corresponding to the winding section 3 of the coil 1. In FIG. 13B and FIG. 13C, the position control of the first lower die 5B and the second lower die 8 was not performed. The inductance values of thirty samples thus made are shown in FIG. 16C.

Figure 16C:
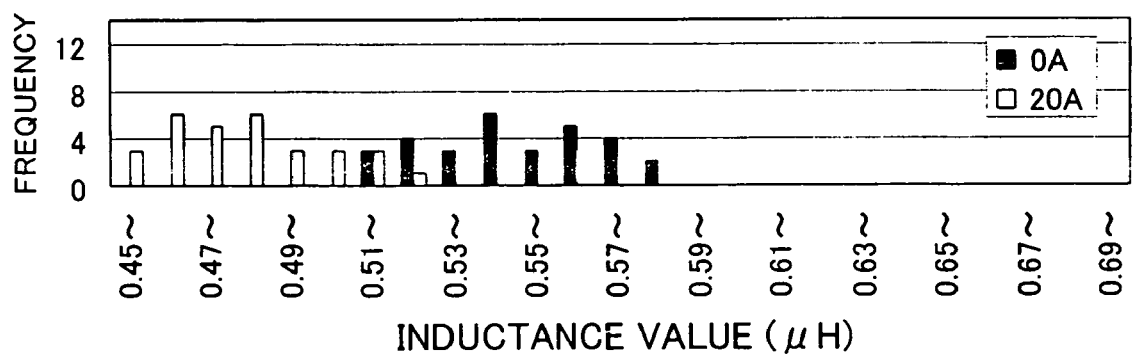

As shown in FIG. 16B, it is understood that variations in inductance values of the samples made in the comparison example 2 are large as the samples made in the comparison example 1 (see FIG. 16C). In concrete, the inductance values in the case with only the alternate current (in the case in which the superposed direct current is 0A) were all in the range from 0.55 to 0.63 μH, and the difference between the minimum value and the maximum value was 0.08 μH. When the direct current of 20A was superposed, the inductance values were all within the range from 0.47to 0.56 μH, and the difference between the minimum value and the maximum vale was 0.09 μH.

Next, the densities of the center parts of the samples were measured with Gamma Densomat made by Creveserge (a density measuring device using γ rays) as in the example 1. As a result, all of the density of the part ② corresponding to the lower surface of the winding section 3 of the coil 1 shown in FIG. 2B, and the density of the part ③ corresponding to the upper surface of the winding section 3 of the coil 1 were 6.4 to 6.5 g/cm³, while the density of the hollow part ① of the coil 1 was 5.0 to 5.4 g/cm³. Namely, it was found out that in the samples made in the example 1, the difference in density between the parts ② and ③ corresponding to the upper and lower surfaces of the winding section 3 of the coil 1 and the part corresponding to the hollow part ① of the coil 1 is only 0.1 g/cm³, while in the samples made in the comparison example 2, the difference in the density between the parts ② and ③ corresponding to the upper and lower surfaces of the winding section 3 of the coil 1 and the part corresponding to the hollow part ① of the coil 1 is large and 1.4 g/cm³ or more.

When the position of the coil 1 was measured from the X-ray projection photograph (made by Shimadzu Corporation), it was recognized that the position of the coil 1 in the compacting direction (thickness direction) was deviated upward or downward from the center in the axial direction of the green body 10.

Example 2

Out of the thirty samples made in the example 1, twenty samples were broken and the densities of the parts corresponding to the winding sections 3 of the coils 1 and the densities of the hollow parts of the coil 1 shown in FIG. 2A were measured using an Archimedean method with silicone oil. The result is shown in Table 1. Since the weight of each part is small, each part was taken out from twenty samples, and was measured together. The specific gravity of silicone oil is 0.817.

TABLE 1

|  | In air (g) | In silicone oil (g) | Density (g/cm$^3$) |
| --- | --- | --- | --- |
| Density of part corresponding to winding section 3 of coil 1 | 8.510 | 7.441 | 6.50 |
| Density of part corresponding to hollow part of coil 1 | 7.249 | 6.327 | 6.42 |

As shown in Table 1, the density of the part corresponding to the winding section 3 of the coil 1 shown in FIG. 2A was 6.50 g/cm$^3$, and the density of the part corresponding to the hollow part of the coil 1 was 6.42 g/cm$^3$. Namely, the difference between the density of the part corresponding to the winding section 3 of the coil 1 and the part corresponding to the hollow part of the coil 1 was only 0.08 g/cm$^3$. From this result, it was confirmed that according to the method which the present invention recommends, the coil-embedded dust core with uniform density in entirety can be obtained.

While the description above refers to embodiments and examples of the present invention, it will be understood that various modifications and changes may be made without limiting thereto within the range of the claims.

As explained thus far, according to the present invention, the coil-embedded dust core which attains a predetermined inductance value (design value) with a small variation in inductance value can be efficiently manufactured. According to the present invention, it is not necessary to increase compression pressure, and therefore deformation of the coil, an insulation failure and the like hardly occur.

What is claimed is:

1. A method for manufacturing a coil-embedded dust core in which an air-core coil is embedded in a green body with use of a die machine comprising a upper die set including an upper die and a top punch ascending and descending inside said upper die, and a lower die set including a lower die and a bottom punch ascending and descending inside said lower die, said method comprising in order steps of:
   (a) charging soft magnetic metal powder including an insulation material, composing said green body, into a cavity of said lower die equipped with a tubular member, which has a top portion in substantially the same shape as the plane shape of said air-core coil, in said bottom punch to be ascendable and descendable;
   (b) placing said air-core coil concentrically with said tubular member in a state in which it ascends to a predetermined position, inside the cavity of said lower die with said soft magnetic metal powder being charged therein;
   (c) lowering said upper die to said lower die, and further charging said soft magnetic metal powder into a cavity of said upper die so as to cover said air-core coil; and
   (d) compacting said soft magnetic metal powder in an axial direction of said air-core coil by relatively lowering said top punch with respect to said bottom punch.

2. The method for manufacturing the coil-embedded dust core according to claim 1, wherein
   said air-core coil is a coil made by winding a flat conductor, including a winding section being insulation coated and end sections led out of said winding section.

3. The method for manufacturing the coil-embedded dust core according to claim 1, wherein
   in said step (d), said upper die, said lower die and said tubular member relatively descend to a predetermined position with respect to said bottom punch while a state in which said end sections of said air-core coil are held between said upper die and said lower die is kept and in synchronism with the movement to relatively lower said top punch with respect to said bottom punch.

4. The method for manufacturing the coil-embedded dust core according to claim 1, wherein
   prior to said step (a), said method further comprises a step of controlling a relative position of said lower die, said bottom punch and said tubular member in a compacting direction according to thickness of said winding section of said air-core coil in the axial direction such that an amount of said soft metal powder charged into a part corresponding to said winding section is kept smaller than an amount of said soft magnetic metal powder charged into the other part that is not corresponding to said winding section, with a lower surface of said winding section downward as a reference.

5. The method for manufacturing the coil-embedded dust core according to claim 4, wherein said other part is a part corresponding to a hollow part of said air-core coil.

6. The method for manufacturing the coil-embedded dust core according to claim 1, wherein in said step (d), a compression ratio of said soft magnetic metal powder in a part corresponding to the maximum number of windings of said winding section and a compression ratio of said soft magnetic metal powder in said other part are equal.

7. The method for manufacturing the coil-embedded dust core according to claim 1, wherein a density of said green body in the vicinity of an upper surface or a lower surface of the part corresponding to the maximum number of windings out of said winding section and a density of said green body in said other part are equal.

* * * * *